United States Patent
Scheller et al.

(10) Patent No.: US 10,213,341 B2
(45) Date of Patent: *Feb. 26, 2019

(54) LASER PROBE WITH A REPLACEABLE OPTIC FIBER

(71) Applicant: Katalyst Surgical, LLC, Chesterfield, MO (US)

(72) Inventors: Gregg D Scheller, Wildwood, MO (US); Matthew N Zeid, Ballwin, MO (US)

(*) Notice: Subject to any disclaimer, the term of this patent is extended or adjusted under 35 U.S.C. 154(b) by 470 days.

This patent is subject to a terminal disclaimer.

(21) Appl. No.: 14/332,698

(22) Filed: Jul. 16, 2014

(65) Prior Publication Data

US 2015/0038950 A1 Feb. 5, 2015

Related U.S. Application Data

(60) Provisional application No. 61/860,482, filed on Jul. 31, 2013.

(51) Int. Cl.
*A61F 9/008* (2006.01)
(52) U.S. Cl.
CPC ...... *A61F 9/00823* (2013.01); *A61F 9/00821* (2013.01); *A61F 2009/00863* (2013.01)
(58) Field of Classification Search
CPC .......................... A61F 9/00823; A61F 9/00821
USPC ............................................................ 606/4
See application file for complete search history.

(56) References Cited

U.S. PATENT DOCUMENTS

| 4,687,293 | A | * | 8/1987 | Randazzo | G02B 6/4402 |
| | | | | | 385/102 |
| 4,870,952 | A | * | 10/1989 | Martinez | A61B 1/00117 |
| | | | | | 362/572 |
| 5,190,050 | A | | 3/1993 | Nitzsche | |
| 5,355,871 | A | | 10/1994 | Hurley et al. | |
| 5,381,782 | A | | 1/1995 | DeLaRama et al. | |
| 5,439,000 | A | | 8/1995 | Gunderson et al. | |

(Continued)

FOREIGN PATENT DOCUMENTS

| EP | 0900547 B1 | 3/1999 |
| WO | WO 2006/091597 A1 | 8/2006 |
| WO | WO 2013/133717 | 9/2013 |

OTHER PUBLICATIONS

Definition of Adjacent. Merriam-Webster Dictionary, retrieved on Jun. 21, 2017; Retrieved from the Internet: <http://www.merriam-webster.com/dictionary/adjacent>.*

(Continued)

*Primary Examiner* — Boniface Nganga
*Assistant Examiner* — Sebastian X Lukjan

(57) ABSTRACT

A laser probe with a replaceable optic fiber may include a reusable handle, a reusable housing tube, a reusable handle adapter, a reusable machine adapter, and a replaceable optic fiber. The handle adapter may interface with a proximal end of the handle. The machine adapter may interface with a surgical machine. The replaceable optic fiber may include an optic fiber having a first optic fiber end and a second optic fiber end, a first connector, and a second connector. The optic fiber may be disposed within the first connector and the second connector. The first connector may be temporarily fixed within the handle adapter and the second connector may be temporarily fixed within the machine adapter.

17 Claims, 27 Drawing Sheets

(56) References Cited

U.S. PATENT DOCUMENTS

| | | |
|---|---|---|
| 5,454,794 A | 10/1995 | Narciso et al. |
| 5,520,222 A | 5/1996 | Chikama |
| 6,123,699 A | 9/2000 | Webster, Jr. |
| 6,126,654 A | 10/2000 | Giba et al. |
| 6,198,974 B1 | 3/2001 | Webster, Jr. |
| 6,488,695 B1 | 12/2002 | Hickingbotham |
| 6,505,530 B2 | 1/2003 | Adler et al. |
| 6,530,913 B1 | 3/2003 | Giba et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 10/2010 | McGowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,968,277 B2 | 1/2015 | Scheller et al. |
| 8,951,245 B2 | 2/2015 | Scheller et al. |
| 9,023,019 B2 | 5/2015 | Scheller et al. |
| 9,023,020 B2 | 5/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0157985 A1 | 7/2005 | McGowan, Sr. et al. |
| 2005/0272975 A1 | 12/2005 | McWeeny et al. |
| 2005/0277874 A1 | 12/2005 | Selkee |
| 2007/0185514 A1 | 8/2007 | Kirchhevel |
| 2009/0018993 A1 | 1/2009 | Dick et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0268234 A1 | 10/2010 | Aho et al. |
| 2011/0028947 A1 | 2/2011 | Scheller et al. |
| 2011/0280653 A1* | 11/2011 | Sjostedt ............ H01R 13/187 403/361 |
| 2012/0116361 A1 | 5/2012 | Hanlon et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1* | 10/2013 | LaConte ............ A61B 17/2909 606/1 |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

* cited by examiner

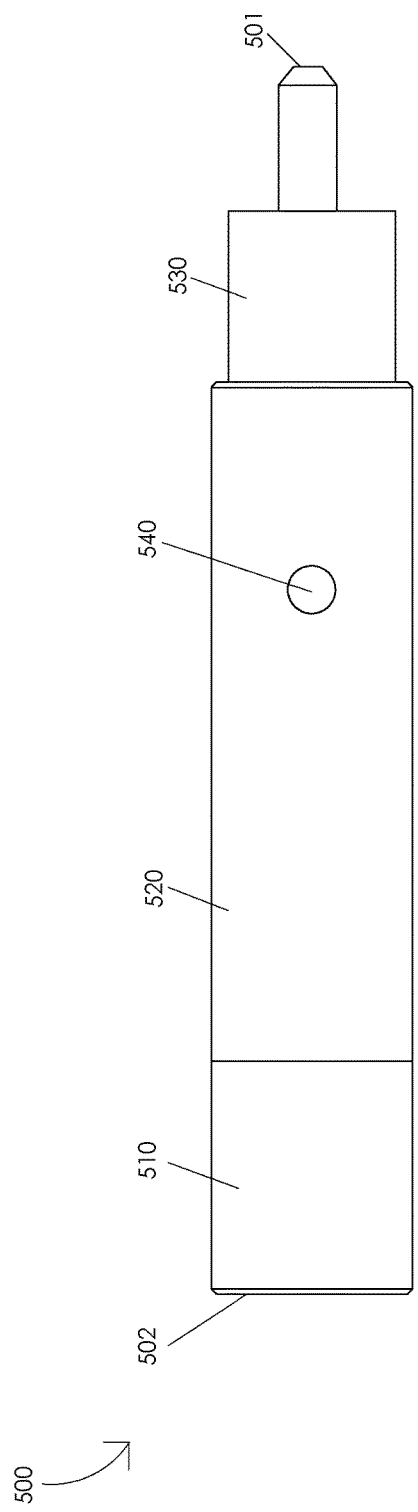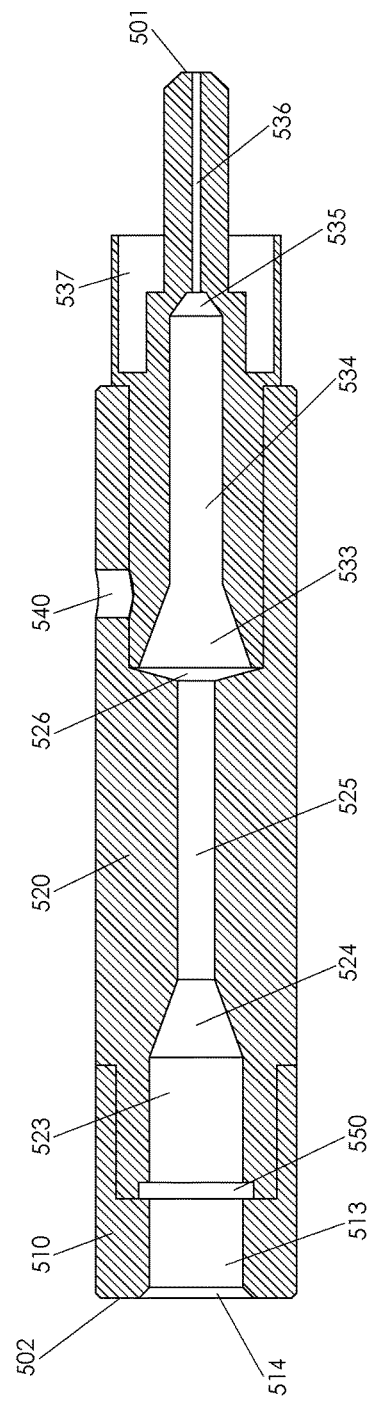
FIG. 5A
FIG. 5B

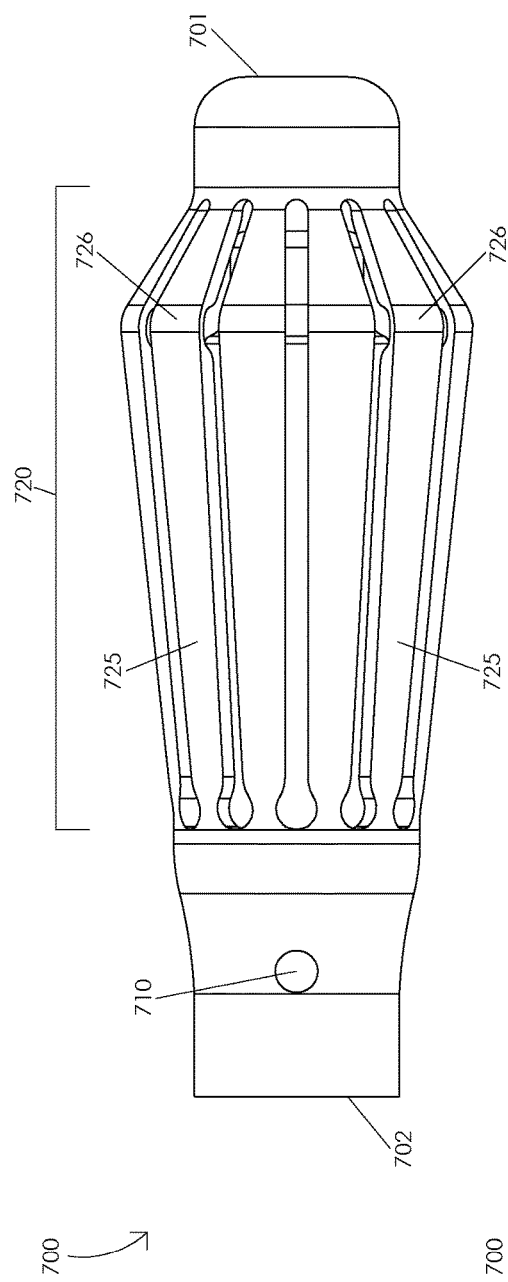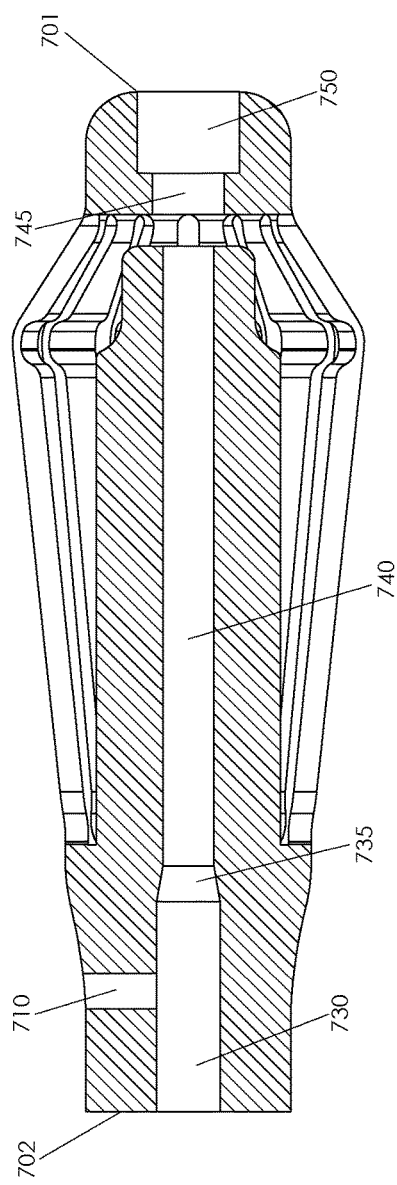
FIG. 7A
FIG. 7B

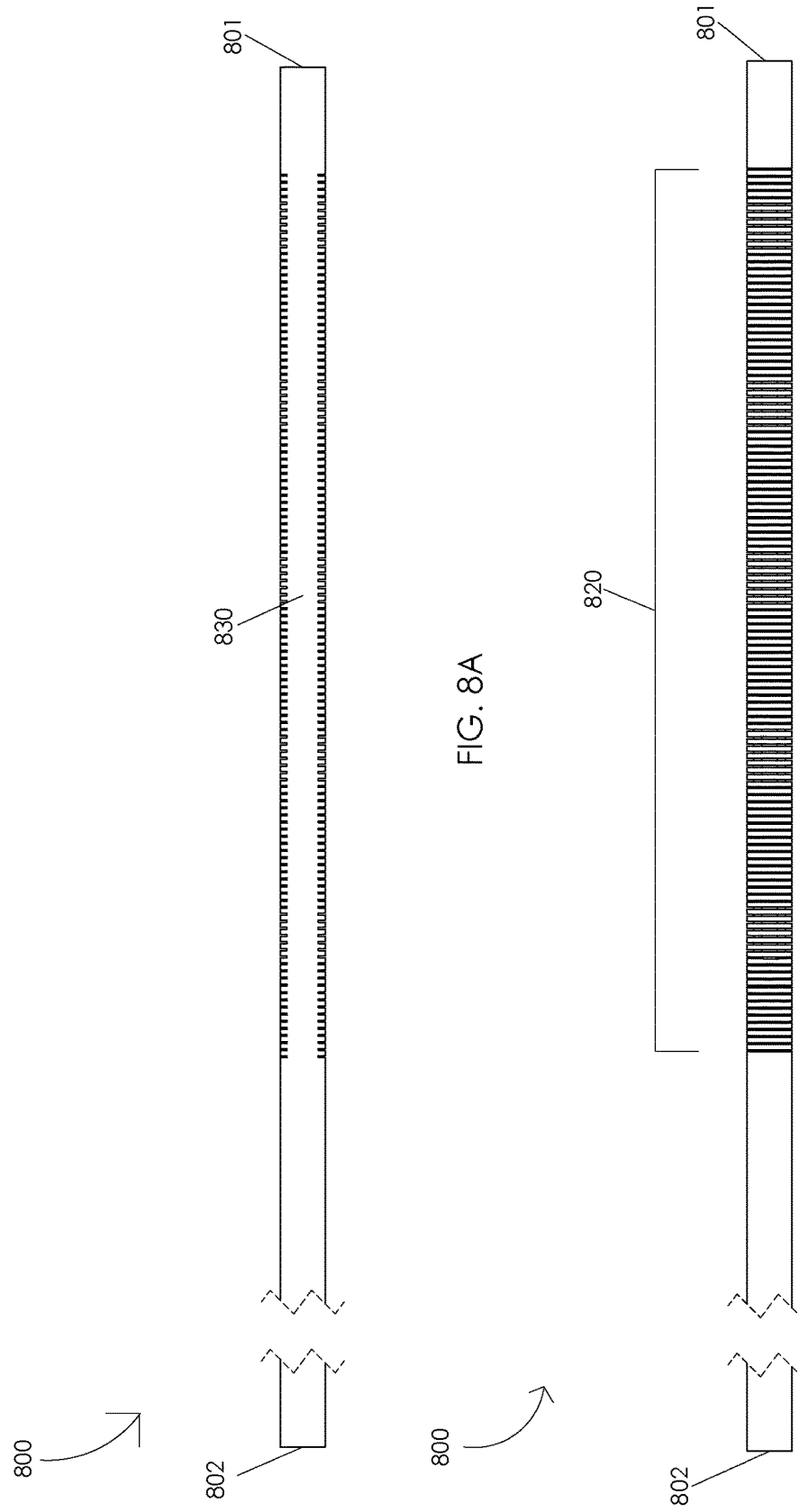

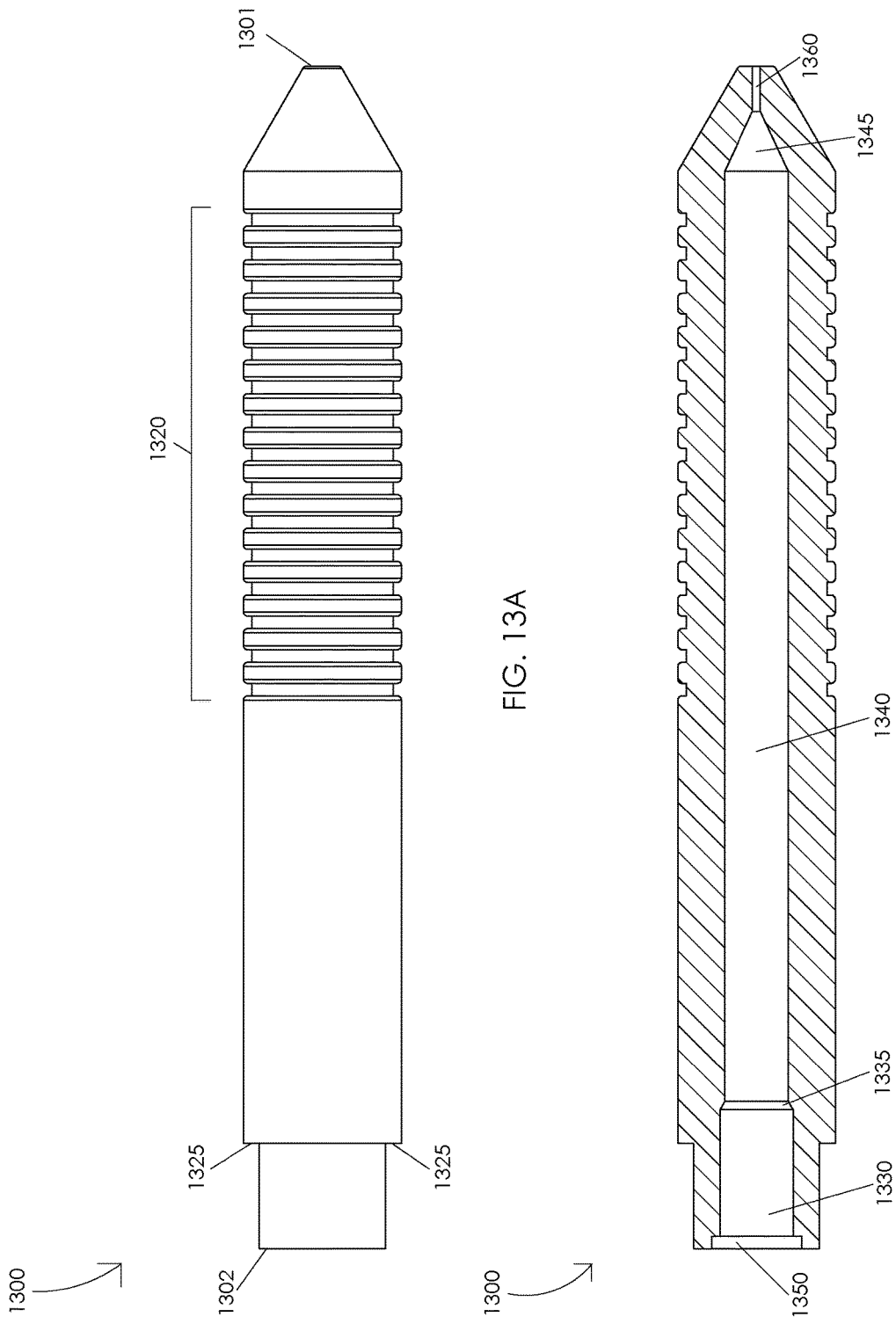

LASER PROBE WITH A REPLACEABLE OPTIC FIBER

CROSS-REFERENCE TO RELATED APPLICATIONS

This application claims the benefit of U.S. Provisional Application No. 61/860,482, filed Jul. 31, 2013.

FIELD OF THE INVENTION

The present disclosure relates to a surgical instrument, and, more particularly, to a laser probe with a replaceable optic fiber.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging. Typically, treatments are performed using a disposable, single-use laser probe connected to a laser surgical machine by an optical fiber. Unfortunately, use of disposable, single-use laser probes increases treatment costs because a new laser probe is required for each surgical treatment. Accordingly, there is a need for a laser probe that may be safely used to perform more than one surgical procedure.

BRIEF SUMMARY OF THE INVENTION

In one or more embodiments, a laser probe with a replaceable optic fiber may comprise a reusable handle having a handle distal end and a handle proximal end, a reusable housing tube having a housing tube distal end and a housing tube proximal end, a reusable handle adapter having a handle adapter distal end and a handle adapter proximal end, a reusable machine adapter having a machine adapter distal end and a machine adapter proximal end, and a replaceable optic fiber. Illustratively, the handle adapter may be configured to interface with the handle proximal end. In one or more embodiments, the machine adapter may be configured to interface with a surgical machine. Illustratively, the replaceable optic fiber may comprise an optic fiber having a first optic fiber end and a second optic fiber end, a first connector having a first connector distal end and a first connector proximal end, and a second connector having a second connector distal end and a second connector proximal end. In one or more embodiments, the optic fiber may be disposed within the first connector and the second connector wherein the first optic fiber end extends a distance from the first connector distal end and the second optic fiber end extends a distance from the second connector distal end. Illustratively, the first connector may be temporarily fixed within the handle adapter and the second connector may be temporarily fixed within the machine adapter.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 5A and 5B are schematic diagrams illustrating a machine adapter;
FIGS. 7A and 7B are schematic diagrams illustrating an actuation handle;
FIGS. 8A, 8B, and 8C are schematic diagrams illustrating a housing tube;
FIGS. 13A and 13B are schematic diagrams illustrating a handle.

DETAILED DESCRIPTION OF AN ILLUSTRATIVE EMBODIMENT

Figure 1A:
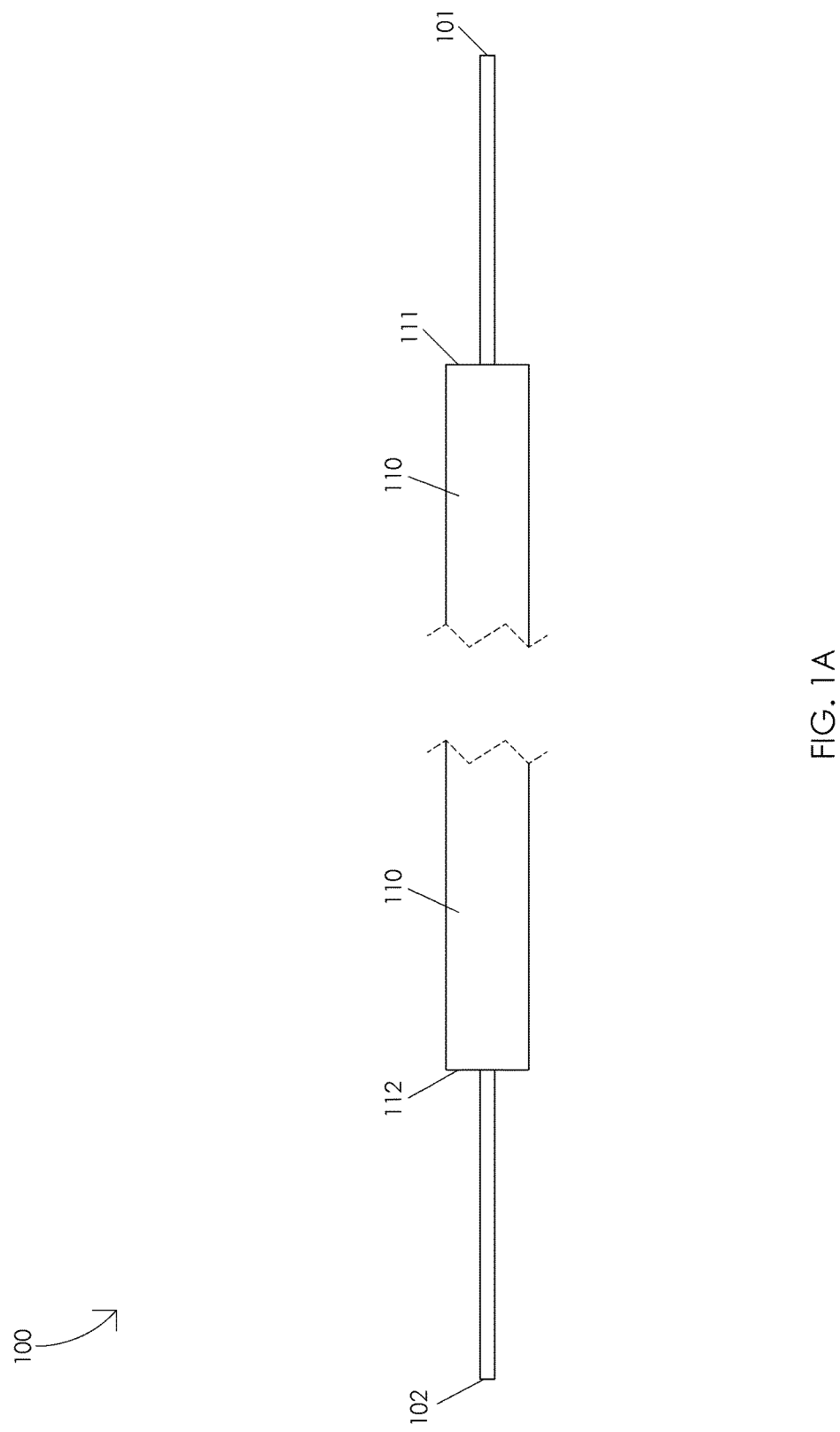
FIGS. 1A and 1B are schematic diagrams illustrating an optic fiber.
Figure 1B:
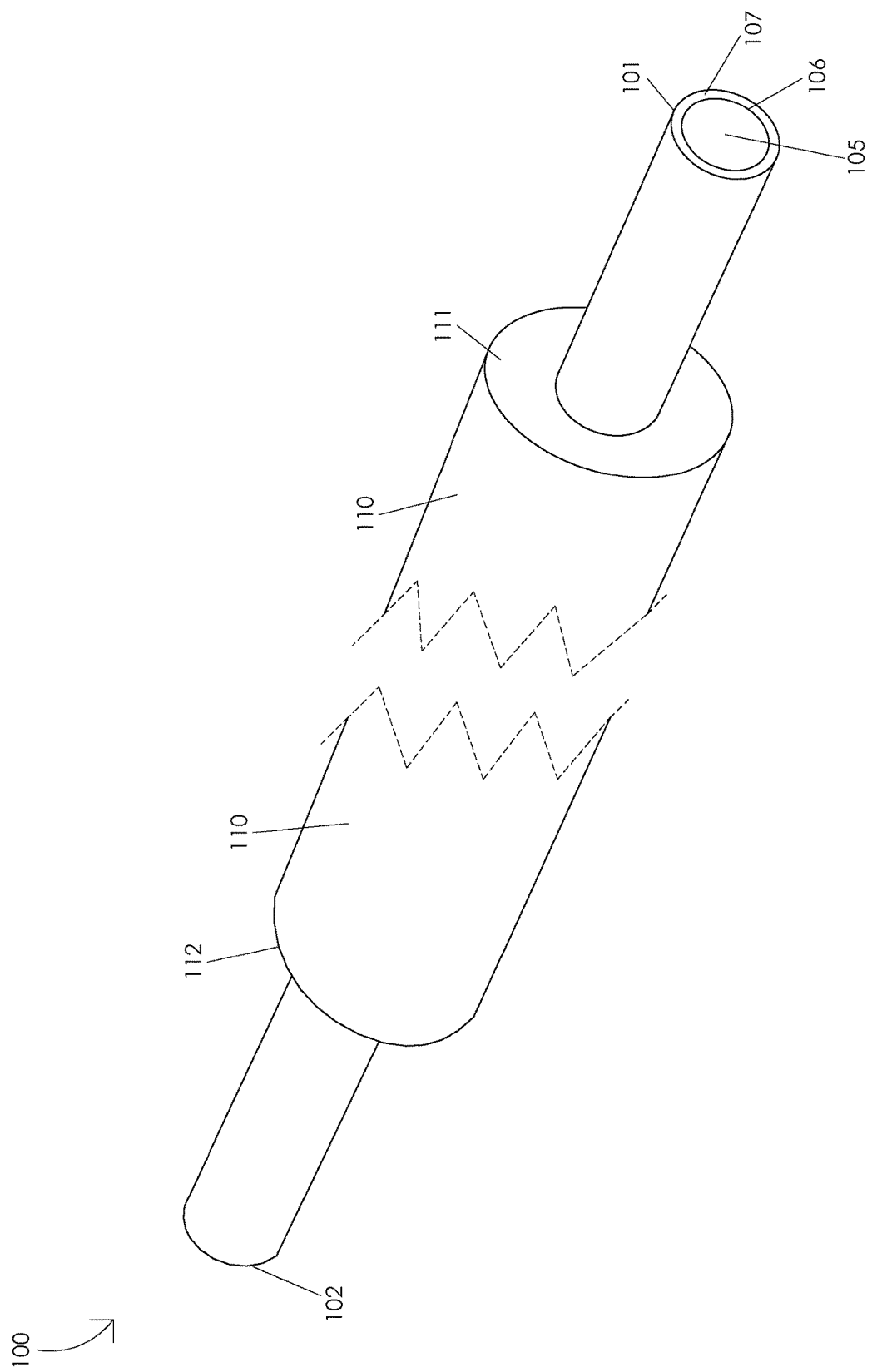

FIGS. 1A and 1B are schematic diagrams illustrating an optic fiber 100. FIG. 1A illustrates a side view of optic fiber 100. Illustratively, optic fiber 100 may comprise an optic fiber distal end 101 and an optic fiber proximal end 102. FIG. 1B illustrates an angled view of optic fiber 100. In one or more embodiments, optic fiber 100 may comprise a core 105, a cladding 106, a buffer 107, and a jacket 110 having a jacket distal end 111 and a jacket proximal end 112. Illustratively, at least a portion of core 105 may be disposed in cladding 106. In one or more embodiments, at least a portion of cladding 106 may be disposed in buffer 107. Illustratively, at least a portion of buffer 107 may be disposed in jacket 110.

In one or more embodiments, jacket 110 may be configured to protect a portion of optic fiber 100. Illustratively, jacket 110 may be configured to prevent damage to one or more properties of optic fiber 100, e.g., jacket 110 may be configured to prevent damage to an optical property of optic fiber 100. For example, jacket 110 may be configured to prevent optic fiber 100 from cracking or breaking. Jacket 110 may be manufactured from any suitable material, e.g., polymers, metals, metal alloys, etc., or from any combination of suitable materials. In one or more embodiments, jacket 110 may be manufactured from silicone. Illustratively, jacket 110 may be manufactured from polyethylene. In one or more embodiments, jacket 110 may be manufactured from polyvinyl chloride. Illustratively, buffer 107 may be configured to protect a portion of optic fiber 100. In one or more embodiments, buffer 107 may be configured to prevent damage to one or more properties of optic fiber 100, e.g., buffer 107 may be configured to prevent damage to an optical property of optic fiber 100. For example, buffer 107 may be configured to prevent optic fiber 100 from cracking or breaking. Buffer 107 may be manufactured from any suitable material, e.g., polymers, metals, metal alloys, etc., or from any combination of suitable materials. In one or more embodiments, buffer 107 may be manufactured from polyimide. Illustratively, buffer 107 may have an outer diameter in a range of 185.0 to 245.0 micrometers, e.g., buffer 107 may have an outer diameter of 195.0 micrometers. In one or more embodiments, buffer 107 may have an outer diameter less than 185.0 micrometers or greater than 245.0 micrometers, e.g., buffer 107 may have an outer diameter of 65.0 micrometers. Illustratively, cladding 106 may be configured to confine light with in core 105 by total internal reflection at the boundary of cladding 106 and core 105. Cladding 106 may be manufactured from any suitable material, e.g., silica, etc. In one or more embodiments, cladding 106 may be manufactured from doped silica. Illustratively, cladding 106 may have an outer diameter in a range of 160.0 to 225.0 micrometers, e.g., cladding 106 may have an outer diameter of 165.0 micrometers. In one or more embodiments, cladding 106 may have an outer diameter less than 160.0 micrometers or greater than 225.0 micrometers, e.g., cladding 106 may have an outer diameter of 55.0 micrometers. Illustratively, core 105 may be configured to transmit light. Core 105 may be manufactured from any suitable material, e.g., glass, plastic, etc. In one or more embodiments, core 105 may be manufactured from silica with a high hydroxyl content. Illustratively, core 105 may have an outer diameter in a range of 145.0 to 205.0 micrometers, e.g., core 105 may have an outer diameter of 150.0 micrometers. In one or more embodiments, core 105 may have an outer diameter less than 145.0 micrometers or greater than 205.0 micrometers, e.g., core 105 may have an outer diameter of 50.0 micrometers.

Figure 2A:
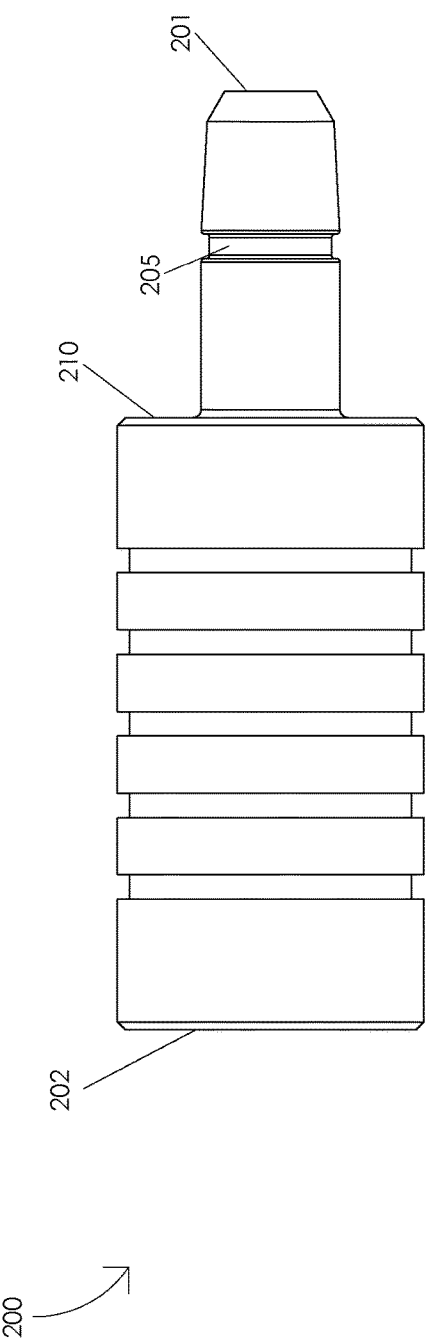
FIGS. 2A and 2B are schematic diagrams illustrating a connector.
Figure 2B:
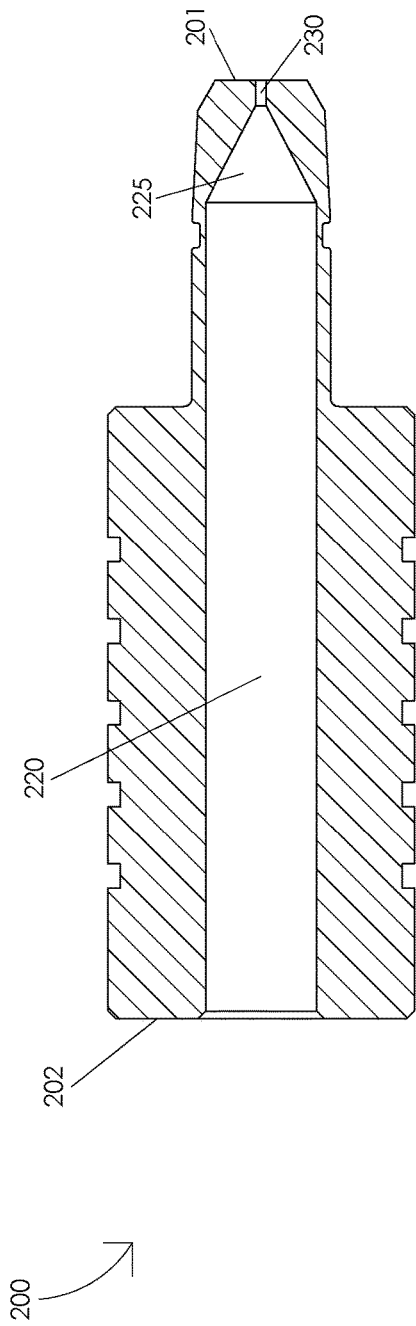

FIGS. 2A and 2B are schematic diagrams illustrating a connector 200. FIG. 2A illustrates a side view of connector 200. Illustratively, connector 200 may comprise a connector distal end 201, a connector proximal end, a temporary fixation channel 205, and an interface 210. FIG. 2B illustrates a cross-sectional view of connector 200. In one or more embodiments, connector 200 may comprise an inner bore 220, a guide cone 225, and an optic fiber housing 230. Connector 200 may be manufactured from any suitable material, e.g., polymers, metals, metal alloys, etc., or from any combination of suitable materials.

Figure 3A:
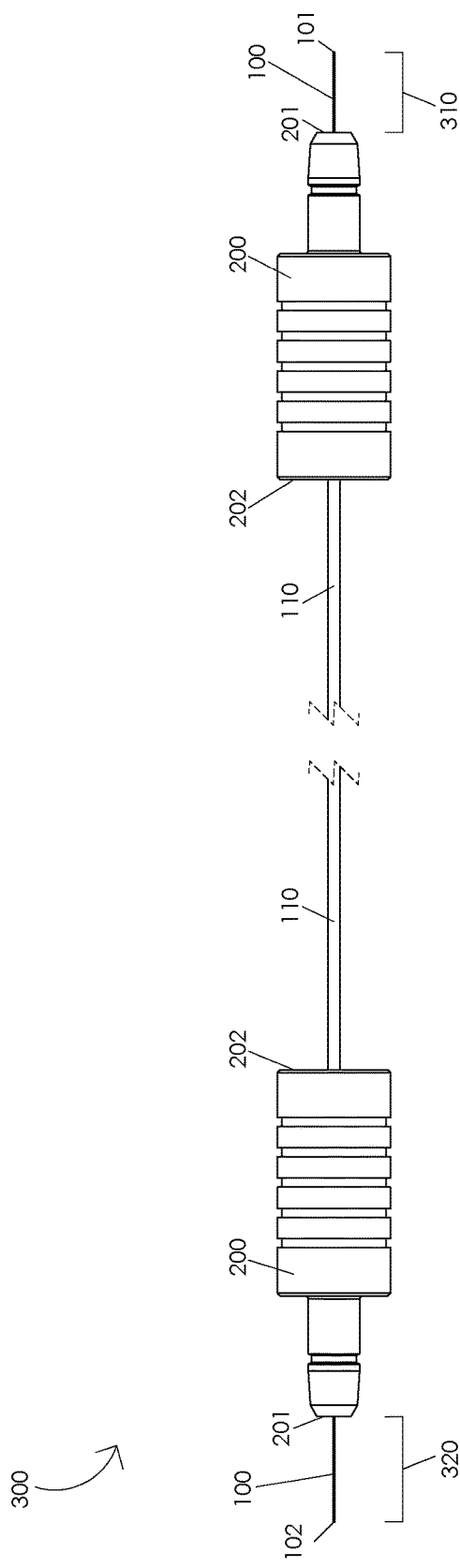
FIGS. 3A and 3B are schematic diagrams illustrating a replaceable optic fiber.
Figure 3B:
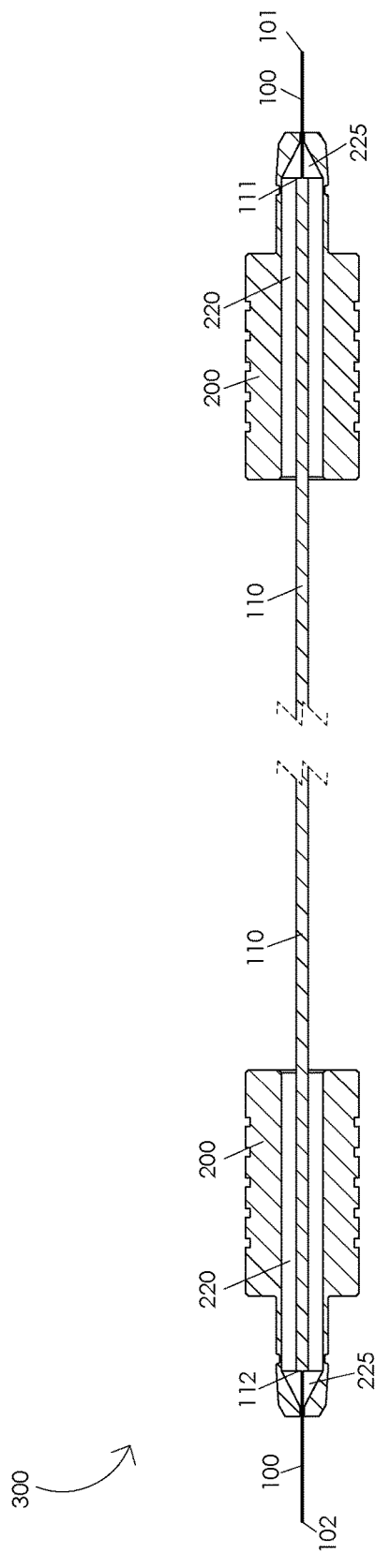

FIGS. 3A and 3B are schematic diagrams illustrating a replaceable optic fiber 300. FIG. 3A illustrates a side view of replaceable optic fiber 300. Illustratively, a replaceable optic fiber 300 may comprise an optic fiber 100 and a pair of connectors 200. FIG. 3B illustrates a cross-sectional view of replaceable optic fiber 300. In one or more embodiments, replaceable optic fiber 300 may be manufactured by threading optic fiber distal end 101 through a first connector 200. Illustratively, replaceable optic fiber 300 may be manufactured by threading optic fiber distal end 101 into inner bore 220 starting from first connector proximal end 202. In one or more embodiments, replaceable optic fiber 300 may be manufactured by threading optic fiber distal end 101 into guide cone 225. Illustratively, guide cone 225 may be configured to guide optic fiber distal end 101 into optic fiber housing 230. In one or more embodiments, replaceable optic fiber 300 may be manufactured by threading optic fiber distal end 101 into optic fiber housing 230. Illustratively, replaceable optic fiber 300 may be manufactured by threading optic fiber distal end 101 out from optic fiber housing 230, e.g., until optic fiber distal end 101 extends a distal extension distance 310 from first connector distal end 201. In one or more embodiments, replaceable optic fiber 300 may be manufactured by threading jacket distal end 111 into inner bore 220. Illustratively, a portion of optic fiber 100 may be fixed to a portion of first connector 200, e.g., when optic fiber distal end 101 extends a distal extension distance 310 from first connector distal end 201. In one or more embodiments, a portion of optic fiber 100 may be fixed within optic fiber housing 230, e.g., when optic fiber distal end 101 extends a distal extension distance 310 from first connector distal end 201. Illustratively, a portion of optic fiber 100 may be fixed to a portion of first connector 200, e.g., by an adhesive or any suitable fixation means. In one or more embodiments, a portion of optic fiber 100 may be fixed to a portion of first connector 200, e.g., by a press fit, by a setscrew, etc. Illustratively, a portion of jacket 110 may be fixed to a portion of first connector 200, e.g., when optic fiber distal end 101 extends a distal extension distance 310 from first connector distal end 201.

In one or more embodiments, replaceable optic fiber 300 may be manufactured by threading optic fiber proximal end 102 through a second connector 200. Illustratively, replaceable optic fiber 300 may be manufactured by threading optic fiber proximal end 102 into inner bore 220 starting from second connector proximal end 202. In one or more embodiments, replaceable optic fiber 300 may be manufactured by threading optic fiber proximal end 102 into guide cone 225. Illustratively, guide cone 225 may be configured to guide optic fiber proximal end 102 into optic fiber housing 230. In one or more embodiments, replaceable optic fiber 300 may be manufactured by threading optic fiber proximal end 102 into optic fiber housing 230. Illustratively, replaceable optic fiber 300 may be manufactured by threading optic fiber proximal end 102 out from optic fiber housing 230, e.g., until optic fiber proximal end 102 extends a proximal extension distance 320 from second connector distal end 201. In one or more embodiments, replaceable optic fiber 300 may be manufactured by threading jacket proximal end 112 into inner bore 220. Illustratively, a portion of optic fiber 100 may be fixed to a portion of second connector 200, e.g., when optic fiber proximal end 102 extends a proximal extension distance 320 from second connector distal end 201. In one or more embodiments, a portion of optic fiber 100 may be fixed within optic fiber housing 230, e.g., when optic fiber proximal end 102 extends a proximal extension distance 320 from second connector distal end 201. Illustratively, a portion of optic fiber 100 may be fixed to a portion of second connector 200, e.g., by an adhesive or any suitable fixation means. In one or more embodiments, a portion of optic fiber 100 may be fixed to a portion of second connector 200, e.g., by a press fit, by a setscrew, etc. Illustratively, a portion of jacket 110 may be fixed to a portion of second connector 200, e.g., when optic fiber proximal end 101 extends a proximal extension distance 320 from second connector distal end 201.

In one or more embodiments, distal extension distance 310 and proximal extension distance 320 may be identical. Illustratively, distal extension distance 310 may be greater than proximal extension distance 320. In one or more embodiments, proximal extension distance 320 may be greater than distal extension distance 310. Illustratively, optic fiber distal end 101 may extend a distal extension distance 310 in a range of 5.0 to 15.0 centimeters from first connector distal end 201, e.g., optic fiber distal end 101 may extend a distal extension distance 310 of 10.5 centimeters from first connector distal end 201. In one or more embodiments, optic fiber distal end 101 may extend a distal extension distance 310 of less than 5.0 centimeters or greater than 15.0 centimeters from first connector distal end 201. Illustratively, optic fiber proximal end 102 may extend a proximal extension distance 320 in a range of 3.0 to 10.0 centimeters from second connector distal end 201, e.g., optic fiber proximal end 102 may extend a proximal extension distance 320 of 5.7 centimeters from second connector distal end 201. In one or more embodiments, optic fiber proximal end 102 may extend a proximal extension distance 320 of less than 3.0 centimeters or greater than 10.0 centimeters from second connector distal end 201.

Figure 4B:
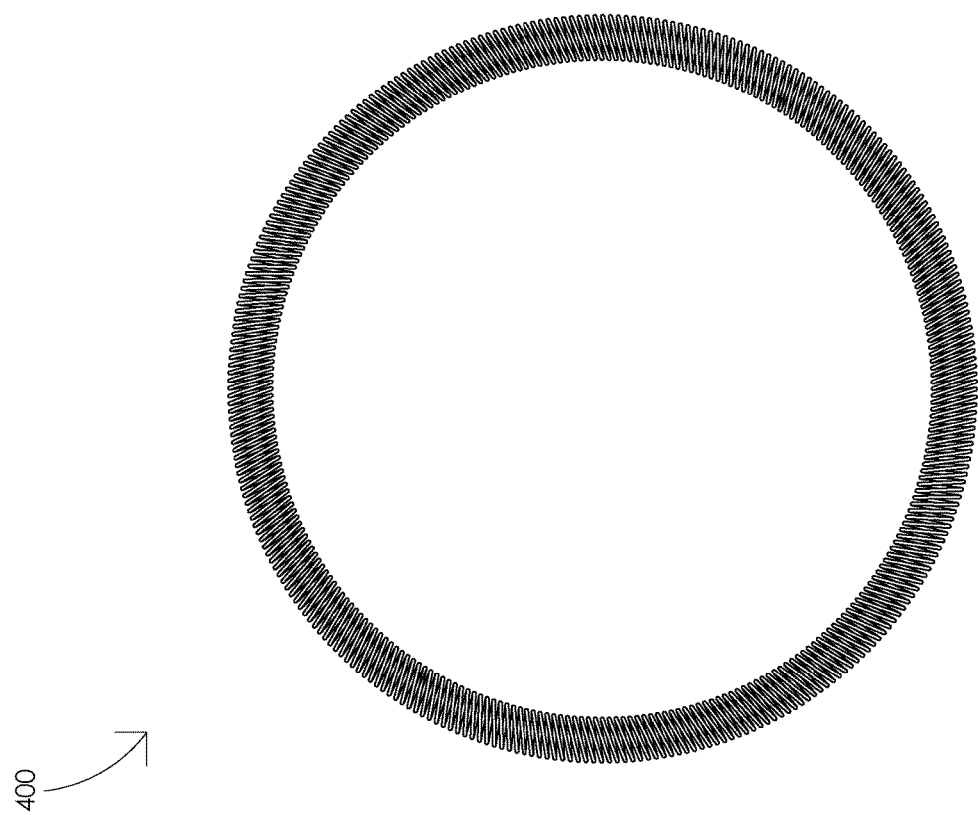
FIGS. 4A and 4B are schematic diagrams illustrating a canted coil spring.
Figure 4A:

FIGS. 4A and 4B are schematic diagrams illustrating a canted coil spring 400.

FIG. 4A illustrates a side view of canted coil spring 400. FIG. 4B illustrates a top view of canted coil spring 400. Canted coil spring 400 may be manufactured from any suitable material, e.g., polymers, metals, metal alloys, etc., or from any combination of suitable materials. In one or more embodiments, canted coil spring 400 may be manufactured from stainless steel. In one or more embodiments, canted coil spring 400 may be manufactured from a material suitable for sterilization by a medical autoclave. Illustratively, canted coil spring 400 may be manufactured from a material, e.g., Nylon, titanium, stainless steel, etc., configured to withstand exposure to temperatures, pressures, and ambient conditions present in a medical autoclave without degradation. For example, canted coil spring 400 may be configured to function normally after exposure in a temperature 250° F. for 15 minutes at an atmospheric pressure of 15 psi. In one or more embodiments, canted coil spring 400 may be configured to be used in a surgical procedure and then sterilized by a medical autoclave at least three times. Illustratively, canted coil spring 400 may be configured to be used in a surgical procedure and then sterilized by a medical autoclave more than three times. In one or more embodiments, canted coil spring 400 may be sterilized in a medical autoclave and then canted coil spring 400 may be used in a first surgical procedure. Illustratively, canted coil spring 400 may be sterilized in a medical autoclave after use in the first surgical procedure and then canted coil spring 400 may be used in a second surgical procedure. In one or more embodiments, canted coil spring 400 may be sterilized in a medical autoclave after use in the second surgical procedure and then canted coil spring 400 may be used in a third surgical procedure.

Illustratively, canted coil spring 400 may comprise a slanted coil spring having a wire diameter in a range of 0.004 to 0.005 inches, e.g., canted coil spring 400 may comprise a slanted coil spring having a wire diameter of 0.0045 inches. In one or more embodiments, canted coil spring 400 may comprise a slanted coil spring having a wire diameter of less than 0.004 inches or greater than 0.005 inches, e.g., canted coil spring 400 may comprise a slanted coil spring having a wire diameter of 0.003 inches. Illustratively, canted coil spring 400 may have a minor coil diameter in a range of 0.02 to 0.03 inches, e.g., canted coil spring 400 may have a minor coil diameter of 0.025 inches. In one or more embodiments, canted coil spring 400 may have a minor coil diameter of less than 0.02 inches or greater than 0.03 inches, e.g., canted coil spring 400 may have a minor coil diameter of 0.035 inches. Illustratively, canted coil spring 400 may have a major coil diameter in a range of 0.026 to 0.031 inches, e.g., canted coil spring 400 may have a major coil diameter of 0.028 inches. In one or more embodiments, canted coil spring 400 may have a major diameter of less than 0.026 inches or greater than 0.031 inches, e.g., canted coil spring 400 may have a major diameter of 0.035 inches.

FIGS. 5A and 5B are schematic diagrams illustrating a machine adapter 500. FIG. 5A illustrates a top view of machine adapter 500. In one or more embodiments, machine adapter 500 may comprise a machine adapter distal end 501, a machine adapter proximal end 502, an end cap 510, a machine adapter base 520, a machine interface 530, and a fixation mechanism housing 540. FIG. 5B illustrates a cross-sectional view of machine adapter 500. Illustratively, machine adapter 500 may comprise an end cap proximal taper 514, an end cap inner bore 513, a canted coil spring housing 550, a machine adapter base proximal chamber 523, a machine adapter base guide cone 524, a machine adapter base inner bore 525, a machine interface housing 526, a machine interface proximal taper 533, a machine interface inner bore 534, a machine interface guide cone 535, an optic fiber proximal end guide 536, and a receiving chamber 537. Machine adapter 500 may be manufactured from any suitable material, e.g., polymers, metals, metal alloys, etc., or from any combination of suitable materials. In one or more embodiments, machine adapter 500 may be manufactured from a material suitable for sterilization by a medical autoclave. Illustratively, machine adapter 500 may be manufactured from a material, e.g., Nylon, titanium, stainless steel, etc., configured to withstand exposure to temperatures, pressures, and ambient conditions present in a medical autoclave without degradation. For example, machine adapter 500 may be configured to function normally after exposure in a temperature 250° F. for 15 minutes at an atmospheric pressure of 15 psi. In one or more embodiments, machine adapter 500 may be configured to be used in a surgical procedure and then sterilized by a medical autoclave at least three times. Illustratively, machine adapter 500 may be configured to be used in a surgical procedure and then sterilized by a medical autoclave more than three times. In one or more embodiments, machine adapter 500 may be sterilized in a medical autoclave and then machine adapter 500 may be used in a first surgical procedure. Illustratively, machine adapter 500 may be sterilized in a medical autoclave after use in the first surgical procedure and then machine adapter 500 may be used in a second surgical procedure. In one or more embodiments, machine adapter 500 may be sterilized in a medical autoclave after use in the second surgical procedure and then machine adapter 500 may be used in a third surgical procedure.

In one or more embodiments, a portion of machine interface 530 may be disposed within machine interface housing 526. Illustratively, a portion of machine interface 530 may be fixed within machine interface housing 526, e.g., by second fixation mechanism 920. In one or more embodiments, a portion of machine interface 530 may be fixed within machine interface housing 526 by any suitable fixation means, e.g., a portion of machine interface 530 may be fixed within machine interface housing 526 by an adhesive, a press fit, a weld, a setscrew, etc. Illustratively, canted coil spring 400 may be disposed within machine adapter 500. In one or more embodiments, canted coil spring 400 may be disposed within canted coil spring housing 550. Illustratively, canted coil spring 400 may be fixed within canted coil spring housing 550. In one or more embodiments, canted coil spring 400 may be fixed within canted coil spring housing 550, e.g., by an adhesive or any suitable fixation means. Illustratively, canted coil spring 400 may be fixed within canted coil spring housing 550, e.g., by a spring force. For example, canted coil spring 400 may be configured to apply a spring force to an outer perimeter of canted coil spring housing 550. In one or more embodiments, a portion of machine adapter base 520 may be disposed within end cap 510. Illustratively, a portion of machine adapter base 520 may be fixed within end cap 510, e.g., by an adhesive or any suitable fixation means. For example, a portion of machine adapter base 520 may be fixed within end cap 510 by a press fit, a weld, a setscrew, etc.

Figure 6A:
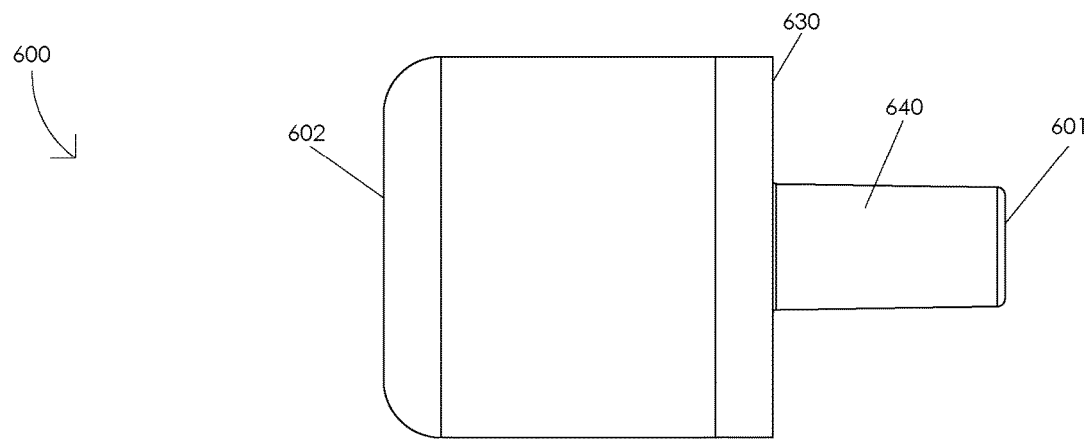
FIGS. 6A and 6B are schematic diagrams illustrating an actuation handle adapter.
Figure 6B:
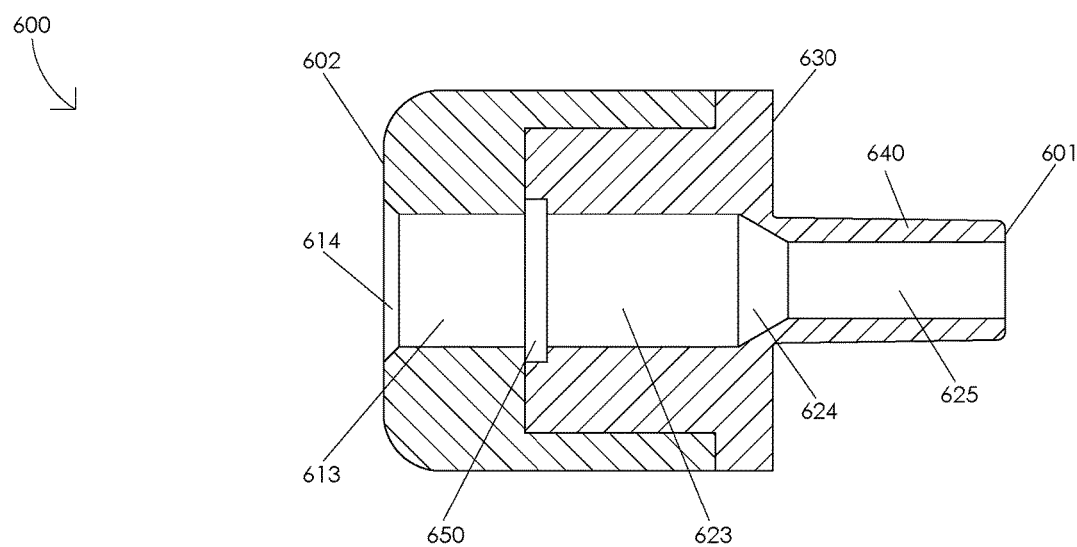

FIGS. 6A and 6B are schematic diagrams illustrating an actuation handle adapter 600. FIG. 6A illustrates a top view of actuation handle adapter 600. In one or more embodiments, actuation handle adapter 600 may comprise an actuation handle adapter distal end 601, an actuation handle adapter proximal end 602, an actuation handle interface 630, and an actuation handle adapter projection 640. FIG. 6B illustrates a cross-sectional view of actuation handle adapter 600. In one or more embodiments, actuation handle adapter 600 may comprise an actuation handle adapter proximal taper 614, an actuation handle adapter proximal chamber 613, a canted coil spring housing 650, an actuation handle adapter inner bore 623, an actuation handle adapter guide cone 624, and an actuation handle adapter distal chamber 625. Illustratively, canted coil spring 400 may be disposed within actuation handle adapter 600. In one or more embodiments, canted coil spring 400 may be disposed within canted coil spring housing 650. Illustratively, canted coil spring 400 may be fixed within canted coil spring housing 650. In one or more embodiments, canted coil spring 400 may be fixed within canted coil spring housing 650, e.g., by an adhesive or any suitable fixation means. Illustratively, canted coil spring 400 may be fixed within canted coil spring housing 650, e.g., by a spring force. For example, canted coil spring 400 may be configured to apply a spring force to an outer perimeter of canted coil spring housing 650.

Actuation handle adapter 600 may be manufactured from any suitable material, e.g., polymers, metals, metal alloys, etc., or from any combination of suitable materials. In one or more embodiments, actuation handle adapter 600 may be manufactured from a material suitable for sterilization by a medical autoclave. Illustratively, actuation handle adapter 600 may be manufactured from a material, e.g., Nylon, titanium, stainless steel, etc., configured to withstand exposure to temperatures, pressures, and ambient conditions present in a medical autoclave without degradation. For example, actuation handle adapter 600 may be configured to function normally after exposure in a temperature 250° F. for 15 minutes at an atmospheric pressure of 15 psi. In one or more embodiments, actuation handle adapter 600 may be configured to be used in a surgical procedure and then sterilized by a medical autoclave at least three times. Illustratively, actuation handle adapter 600 may be configured to be used in a surgical procedure and then sterilized by a medical autoclave more than three times. In one or more embodiments, actuation handle adapter 600 may be sterilized in a medical autoclave and then actuation handle adapter 600 may be used in a first surgical procedure. Illustratively, actuation handle adapter 600 may be sterilized in a medical autoclave after use in the first surgical procedure and then actuation handle adapter 600 may be used in a second surgical procedure. In one or more embodiments, actuation handle adapter 600 may be sterilized in a medical autoclave after use in the second surgical procedure and then actuation handle adapter 600 may be used in a third surgical procedure.

FIGS. 7A and 7B are schematic diagrams illustrating an actuation handle 700. FIG. 7A illustrates a top view of actuation handle 700. In one or more embodiments, actuation handle 700 may comprise an actuation handle distal end 701, an actuation handle proximal end 702, a fixation mechanism housing 710, and an actuation structure 720. Illustratively, actuation structure 720 may comprise a plurality of actuation arms 725. In one or more embodiments, each actuation arm 725 may comprise at least one extension mechanism 726. In one or more embodiments, actuation structure 720 may comprise a shape memory material configured to project actuation handle distal end 701 a first distance from actuation handle proximal end 702, e.g., when actuation structure 720 is fully decompressed. Illustratively, actuation structure 720 may comprise a shape memory material configured to project actuation handle distal end 701 a second distance from actuation handle proximal end 702, e.g., when actuation structure 720 is fully compressed. In one or more embodiments, the second distance from actuation handle proximal end 702 may be greater than the first distance from actuation handle proximal end 702. Actuation structure 720 may be manufactured from any suitable material, e.g., polymers, metals, metal alloys, etc., or from any combination of suitable materials.

Illustratively, actuation structure 720 may be compressed by an application of a compressive force to actuation structure 720. In one or more embodiments, actuation structure 720 may be compressed by an application of one or more compressive forces located at one or more locations around an outer perimeter of actuation structure 720. Illustratively, the one or more locations may comprise any of a plurality of locations around the outer perimeter of actuation structure 720. For example, a surgeon may compress actuation structure 720 by squeezing actuation structure 720. Illustratively, the surgeon may compress actuation structure 720 by squeezing actuation structure 720 at any particular location of a plurality of locations around an outer perimeter of actuation structure 720. For example, a surgeon may rotate actuation handle 700 and compress actuation structure 720 from any rotational position of a plurality of rotational positions of actuation handle 700.

In one or more embodiments, actuation structure 720 may be compressed by an application of a compressive force to any one or more of the plurality of actuation arms 725. Illustratively, each actuation arm 725 may be configured to actuate independently. In one or more embodiments, each actuation arm 725 may be connected to one or more of the plurality of actuation arms 725 wherein an actuation of a particular actuation arm 725 may be configured to actuate every actuation arm 725 of the plurality of actuation arms 725. Illustratively, one or more actuation arms 725 may be configured to actuate in pairs or groups. For example, an actuation of a first actuation arm 725 may be configured to actuate a second actuation arm 725. In one or more embodiments, a compression of actuation structure 720, e.g., due to an application of a compressive force to a particular actuation arm 725, may be configured to actuate the particular actuation arm 725. Illustratively, an actuation of the particular actuation arm 725 may be configured to actuate every actuation arm 725 of the plurality of actuation arms 725. In one or more embodiments, an application of a compressive force to a particular actuation arm 725 may be configured to extend at least one extension mechanism 726 of the particular actuation arm 725.

FIG. 7B illustrates a cross-sectional view of actuation handle 700. In one or more embodiments, actuation handle 700 may comprise an actuation handle adapter housing 730, an actuation handle guide cone 735, an actuation handle inner bore 740, an actuation handle distal chamber 745, and an inner nosecone housing 750. Actuation handle 700 may be manufactured from any suitable material, e.g., polymers, metals, metal alloys, etc., or from any combination of suitable materials. In one or more embodiments, actuation handle 700 may be manufactured from a material suitable for sterilization by a medical autoclave. Illustratively, actuation handle 700 may be manufactured from a material, e.g., Nylon, configured to withstand exposure to temperatures, pressures, and ambient conditions present in a medical autoclave without degradation. For example, actuation handle 700 may be configured to function normally after exposure in a temperature 250° F. for 15 minutes at an atmospheric pressure of 15 psi. In one or more embodiments, actuation handle 700 may be configured to be used in a surgical procedure and then sterilized by a medical autoclave at least three times. Illustratively, actuation handle 700 may be configured to be used in a surgical procedure and then sterilized by a medical autoclave more than three times. In one or more embodiments, actuation handle 700 may be sterilized in a medical autoclave and then actuation handle 700 may be used in a first surgical procedure. Illustratively, actuation handle 700 may be sterilized in a medical autoclave after use in the first surgical procedure and then actuation handle 700 may be used in a second surgical procedure. In one or more embodiments, actuation handle 700 may be sterilized in a medical autoclave after use in the second surgical procedure and then actuation handle 700 may be used in a third surgical procedure.

Figure 8C:
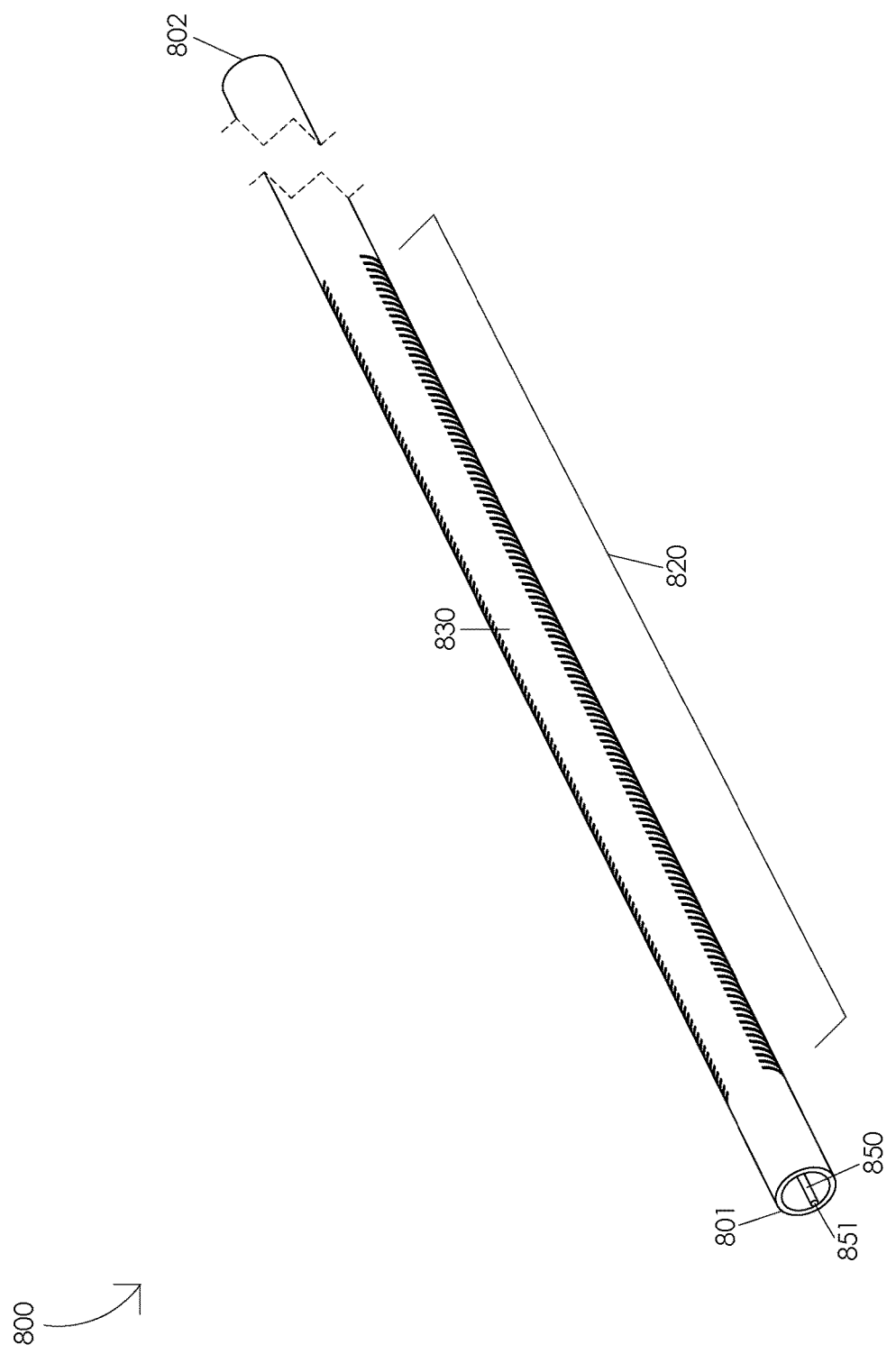

FIGS. 8A, 8B, and 8C are schematic diagrams illustrating a housing tube 800. In one or more embodiments, housing tube 800 may comprise a housing tube distal end 801 and a housing tube proximal end 802. Housing tube 800 may be manufactured from any suitable material, e.g., polymers, metals, metal alloys, etc., or from any combination of suitable materials. Illustratively, housing tube 800 may be manufactured with dimensions configured for microsurgical procedures, e.g., ophthalmic surgical procedures. In one or more embodiments, housing tube 800 may be manufactured from a material suitable for sterilization by a medical autoclave. Illustratively, housing tube 800 may be manufactured from a material, e.g., nitinol, stainless steel, etc., configured to withstand exposure to temperatures, pressures, and ambient conditions present in a medical autoclave without degradation. For example, housing tube 800 may be configured to function normally after exposure in a temperature 250° F. for 15 minutes at an atmospheric pressure of 15 psi. In one or more embodiments, housing tube 800 may be configured to be used in a surgical procedure and then sterilized by a medical autoclave at least three times. Illustratively, housing tube 800 may be configured to be used in a surgical procedure and then sterilized by a medical autoclave more than three times. In one or more embodiments, housing tube 800 may be sterilized in a medical autoclave and then housing tube 800 may be used in a first surgical procedure. Illustratively, housing tube 800 may be sterilized in a medical autoclave after use in the first surgical procedure and then housing tube 800 may be used in a second surgical procedure. In one or more embodiments, housing tube 800 may be sterilized in a medical autoclave after use in the second surgical procedure and then housing tube 800 may be used in a third surgical procedure.

FIG. 8B illustrates a housing tube 800 oriented to illustrate a first housing tube portion 820. Illustratively, first housing tube portion 820 may have a first stiffness. FIG. 8A illustrates a housing tube 800 oriented to illustrate a second housing tube portion 830. Illustratively, second housing tube portion 830 may have a second stiffness. In one or more embodiments, the second stiffness may be greater than the first stiffness. Illustratively, first housing tube portion 820 may comprise a first material having a first stiffness. In one or more embodiments, second housing tube portion 830 may comprise a second material having a second stiffness. Illustratively, the second stiffness may be greater than the first stiffness.

In one or more embodiments, housing tube 800 may comprise a non-uniform inner diameter or a non-uniform outer diameter, e.g., to vary a stiffness of one or more portions of housing tube 800. Illustratively, a first housing tube portion 820 may comprise a first inner diameter of housing tube 800 and a second housing tube portion 830 may comprise a second inner diameter of housing tube 800. In one or more embodiments, the first inner diameter of housing tube 800 may be larger than the second inner diameter of housing tube 800. Illustratively, a first housing tube portion 820 may comprise a first outer diameter of housing tube 800 and a second housing tube portion 830 may comprise a second outer diameter of housing tube 800. In one or more embodiments, the first outer diameter of housing tube 800 may be smaller than the second outer diameter of housing tube 800.

In one or more embodiments, first housing tube portion 820 may comprise one or more apertures configured to produce a first stiffness of first housing tube portion 820. Illustratively, second housing tube portion 830 may comprise a solid portion of housing tube 800 having a second stiffness. In one or more embodiments, the second stiffness may be greater than the first stiffness. Illustratively, first housing tube portion 820 may comprise one or more apertures configured to produce a first stiffness of first housing tube portion 820. In one or more embodiments, second housing tube portion 830 may comprise one or more apertures configured to produce a second stiffness of second housing tube portion 830. Illustratively, the second stiffness may be greater than the first stiffness.

In one or more embodiments, first housing tube portion 820 may comprise a plurality of slits configured to separate one or more solid portions of housing tube 800. Illustratively, a plurality of slits may be cut, e.g., laser cut, into first housing tube portion 820. For example, a plurality of slits may be cut, e.g., by an electric discharge machine, into first housing tube portion 820. In one or more embodiments, first housing tube portion 820 may comprise a plurality of slits configured to minimize a force of friction between housing tube 800 and a cannula, e.g., as housing tube 800 is inserted into the cannula or as housing tube 800 is extracted from the cannula. For example, each slit of the plurality of slits may comprise one or more arches configured to minimize a force of friction between housing tube 800 and a cannula.

FIG. 8C illustrates an angled view of housing tube 800. Illustratively, a cable 850 may be disposed within housing tube 800. In one or more embodiments, cable 850 may comprise a cable distal end 851 and a cable proximal end 852. Illustratively, cable 850 may be disposed within housing tube 800 wherein cable distal end 851 may be adjacent to housing tube distal end 801. In one or more embodiments, cable 850 may be disposed within housing tube 800 wherein a portion of cable 850 may be adjacent to a portion of first housing tube portion 820. Illustratively, a portion of cable 850 may be fixed to a portion of housing tube 800, e.g., by an adhesive or any suitable fixation means. For example, a portion of cable 850 may be fixed to housing tube 800 by a weld, a loop, a tie, etc.

Figure 9:
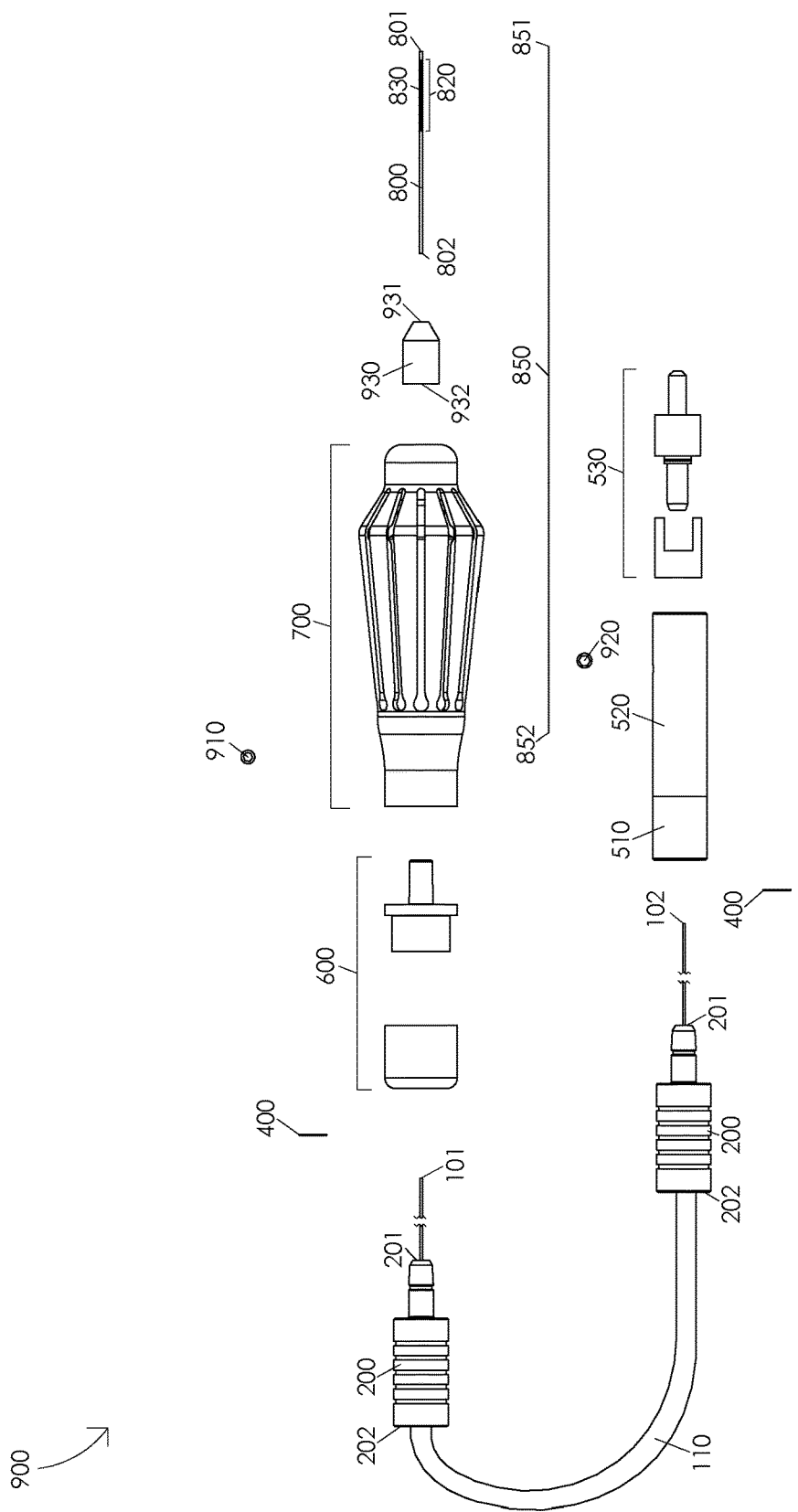
FIG. 9 is a schematic diagram illustrating an exploded view of a steerable laser probe with a replaceable optic fiber assembly.

FIG. 9 is a schematic diagram illustrating an exploded view of a steerable laser probe with a replaceable optic fiber assembly 900. In one or more embodiments, a steerable laser probe with a replaceable optic fiber assembly 900 may comprise a machine adapter 500, a replaceable fiber 300, an actuation handle adapter 600, an actuation handle 700, an inner nosecone 930 having an inner nosecone distal end 931 and an inner nosecone proximal end 902, a housing tube 800, a cable 850 having a cable distal end 851 and a cable proximal end 852, a first fixation mechanism 910, and a second fixation mechanism 920. Inner nosecone 930 may be manufactured from any suitable material, e.g., polymers, metals, metal alloys, etc., or from any combination of suitable materials. Illustratively, inner nosecone 930 may be manufactured with dimensions configured for microsurgical procedures, e.g., ophthalmic surgical procedures. In one or more embodiments, inner nosecone 930 may be manufactured from a material suitable for sterilization by a medical autoclave. Illustratively, inner nosecone 930 may be manufactured from a material, e.g., nitinol, stainless steel, etc., configured to withstand exposure to temperatures, pressures, and ambient conditions present in a medical autoclave without degradation. For example, inner nosecone 930 may be configured to function normally after exposure in a temperature 250° F. for 15 minutes at an atmospheric pressure of 15 psi. In one or more embodiments, inner nosecone 930 may be configured to be used in a surgical procedure and then sterilized by a medical autoclave at least three times. Illustratively, inner nosecone 930 may be configured to be used in a surgical procedure and then sterilized by a medical autoclave more than three times. In one or more embodiments, inner nosecone 930 may be sterilized in a medical autoclave and then inner nosecone 930 may be used in a first surgical procedure. Illustratively, inner nosecone 930 may be sterilized in a medical autoclave after use in the first surgical procedure and then inner nosecone 930 may be used in a second surgical procedure. In one or more embodiments, inner nosecone 930 may be sterilized in a medical autoclave after use in the second surgical procedure and then inner nosecone 930 may be used in a third surgical procedure.

Illustratively, a portion of replaceable optic fiber 300 may be disposed within machine adapter 500. In one or more embodiments, optic fiber proximal end 102 may be threaded through machine adapter 500. Illustratively, a portion of replaceable optic fiber 300 may be disposed within machine adapter 500, e.g., optic fiber proximal end 102 may be actuated into end cap proximal taper 514. In one or more embodiments, optic fiber proximal end 102 may be actuated out from end cap proximal taper 514, e.g., optic fiber proximal end 102 may be actuated into end cap inner bore 513. Illustratively, optic fiber proximal end 102 may be actuated out from end cap inner bore 513, e.g., optic fiber proximal end 102 may be actuated into canted coil spring housing 550. In one or more embodiments, optic fiber proximal end 102 may be actuated out from canted coil spring housing 550, e.g., optic fiber proximal end 102 may be actuated into machine adapter base proximal chamber 523. Illustratively, optic fiber proximal end 102 may be actuated out from machine adapter base proximal chamber 523, e.g., optic fiber proximal end 102 may be actuated into machine adapter base guide cone 524. In one or more embodiments, machine adapter base guide cone 524 may be configured to guide a portion of replaceable optic fiber 300 into machine adapter base inner bore 525. Illustratively, optic fiber proximal end 102 may be actuated out from machine adapter base guide cone 524, e.g., optic fiber proximal end 102 may be actuated into machine adapter base inner bore 525. In one or more embodiments, optic fiber proximal end 102 may be actuated out from machine adapter base inner bore 525, e.g., optic fiber proximal end 102 may be actuated into machine interface proximal taper 533. Illustratively, optic fiber proximal end 102 may be actuated out from machine interface proximal taper 533, e.g., optic fiber proximal end 102 may be actuated into machine interface inner bore 534. In one or more embodiments, optic fiber proximal end 102 may be actuated out from machine interface inner bore 534, e.g., optic fiber proximal end 102 may be actuated into machine interface guide cone 535. Illustratively, machine interface guide cone 535 may be configured to guide a portion of replaceable optic fiber 300 into optic fiber proximal end guide 536. In one or more embodiments, optic fiber proximal end 102 may be actuated out from machine interface guide cone 535, e.g., optic fiber proximal end 102 may be actuated into optic fiber proximal end guide 536. For example, a portion of replaceable optic fiber 300 may be disposed within machine adapter 500 wherein optic fiber proximal end 102 may be adjacent to machine adapter distal end 501.

In one or more embodiments, a portion of second connector 200 may be disposed within machine adapter 500. Illustratively, second connector distal end 201 may be actuated into machine adapter 500. In one or more embodiments, second connector distal end 201 may be actuated into end cap proximal taper 514. Illustratively, second connector distal end 201 may be actuated out from end cap proximal taper 514, e.g., second connector distal end 201 may be actuated into end cap inner bore 513. In one or more embodiments, second connector distal end 201 may be actuated out from end cap inner bore 513, e.g., second connector distal end 201 may be actuated into machine adapter base proximal chamber 523. Illustratively, a portion of second connector 200 may be temporarily fixed within machine adapter 500. In one or more embodiments, canted coil spring 400 may be configured to temporarily fix a portion of second connector 200 within machine adapter 500. Illustratively, as second connector distal end 201 is actuated into machine adapter base proximal chamber 523, canted coil spring 400 may interface with a portion of second connector 200, e.g., canted coil spring 400 may interface with temporary fixation channel 205. In one or more embodiments, an interface between canted coil spring 400 and temporary fixation channel 205 may be configured to temporarily fix a portion of second connector 200 within machine adapter 500. Illustratively, a portion of second connector 200 may be temporarily fixed within machine adapter 500, e.g., by a spring force or any suitable temporary fixation means.

In one or more embodiments, a portion of actuation handle adapter 600 may be disposed within actuation handle 700, e.g., actuation handle interface 630 may be configured to interface with actuation handle proximal end 702. Illustratively, actuation handle adapter distal end 601 may be disposed within actuation handle 700. In one or more embodiments, actuation handle adapter projection 640 may be disposed within actuation handle 700. Illustratively, a portion of actuation handle adapter 600 may be disposed within actuation handle adapter housing 730. In one or more embodiments, actuation handle adapter projection 640 may be disposed within actuation handle adapter housing 730.

Illustratively, a portion of actuation handle adapter 600 may be fixed within a portion of actuation handle 700, e.g., actuation handle adapter projection 640 may be fixed within actuation handle adapter housing 730. In one or more embodiments, first fixation mechanism 910 may be configured to fix actuation handle adapter projection 640 within actuation handle adapter housing 730, e.g., first fixation mechanism 910 may be disposed within fixation mechanism housing 710. For example, first fixation mechanism 910 may comprise a setscrew configured to fix a portion of actuation handle adapter 600 within actuation handle 700. Illustratively, actuation handle adapter projection 640 may be fixed within actuation handle adapter housing 730, e.g., by an adhesive or any suitable fixation means. For example, a portion of actuation handle adapter 600 may be fixed within actuation handle 700 by a press fit, a weld, a setscrew, etc.

In one or more embodiments, a portion of inner nosecone 930 may be disposed within actuation handle 700, e.g., inner nosecone proximal end 932 may be disposed within inner nosecone housing 750. Illustratively, a portion of inner nosecone 930 may be fixed within actuation handle 700, e.g., inner nosecone proximal end 932 may be fixed within inner nosecone housing 750. In one or more embodiments, inner nosecone proximal end 932 may be fixed within inner nosecone housing 750, e.g., by an adhesive or any suitable fixation means. Illustratively, inner nosecone proximal end 932 may be fixed within inner nosecone housing 750 by a press fit, a setscrew, a weld, etc.

In one or more embodiments, a portion of housing tube 800 may be disposed within a portion of inner nosecone 930, e.g., housing tube proximal end 802 may be disposed within inner nosecone 930. Illustratively, a portion of housing tube 800 may be fixed within inner nosecone 930, e.g., housing tube proximal end 802 may be fixed within inner nosecone 930. In one or more embodiments, a portion of housing tube 800 may be fixed within inner nosecone 930, e.g., by an adhesive or any suitable fixation means. Illustratively, a portion of housing tube 800 may be fixed within inner nosecone 930 by a press fit, a setscrew, a weld, etc. In one or more embodiments, cable 850 may be disposed within housing tube 800 and actuation handle 700. For example, cable 850 may be disposed within housing tube 800 wherein cable distal end 851 may be adjacent to housing tube distal end 801. Illustratively, a portion of cable 850 may be fixed within housing tube 800, e.g., by an adhesive or any suitable fixation means. In one or more embodiments, a portion of cable 850 may be fixed within housing tube 800 by a tie, a loop, a weld, etc. For example, cable distal end 851 may be fixed within housing tube 800 by a laser weld or any suitable fixation means. Illustratively, a portion of cable 850 may be fixed within actuation handle 700, e.g., by an adhesive or any suitable fixation means. In one or more embodiments, a portion of cable 850 may be fixed within actuation handle 700 by a tie, a setscrew, a weld, etc. Illustratively, cable proximal end 852 may be fixed within actuation handle 700, e.g., cable proximal end 852 may be disposed within fixation mechanism housing 710. In one or more embodiments, first fixation mechanism 910 may be configured to fix a portion of cable 850 within fixation mechanism housing 710, e.g., first fixation mechanism 910 may be configured to fix cable proximal end 852 within fixation mechanism housing 710.

Illustratively, a portion of replaceable optic fiber 300 may be disposed within actuation handle adapter 600, e.g., a portion of replaceable fiber 300 may be disposed within actuation handle 700. In one or more embodiments, optic fiber distal end 101 may be threaded through actuation handle adapter 600, e.g., optic fiber distal end 101 may be threaded into actuation handle adapter proximal end 602. Illustratively, a portion of replaceable optic fiber 300 may be disposed within actuation handle adapter 600, e.g., optic fiber distal end 101 may be actuated into actuation handle adapter proximal taper 614. In one or more embodiments, optic fiber distal end 101 may be actuated out from actuation handle adapter proximal taper 614, e.g., optic fiber distal end 101 may be actuated into actuation handle adapter proximal chamber 613. Illustratively, optic fiber distal end 101 may be actuated out from actuation handle adapter proximal chamber 613, e.g., optic fiber distal end 101 may be actuated into canted coil spring housing 650. In one or more embodiments, optic fiber distal end 101 may be actuated out from canted coil spring housing 650, e.g., optic fiber distal end 101 may be actuated into actuation handle adapter inner bore 623. Illustratively, optic fiber distal end 101 may be actuated out from actuation handle adapter inner bore 623, e.g., optic fiber distal end 101 may be actuated into actuation handle adapter guide cone 624. In one or more embodiments, actuation handle adapter guide cone 624 may be configured to guide a portion of replaceable optic fiber 300 into actuation handle adapter distal chamber 625. Illustratively, optic fiber distal end 101 may be actuated out from actuation handle adapter guide cone 624, e.g., optic fiber distal end 101 may be actuated into actuation handle adapter distal chamber 625. In one or more embodiments, actuation handle adapter guide cone 624 may be configured to guide a portion of replaceable optic fiber 300 into actuation handle adapter housing 730. Illustratively, optic fiber distal end 101 may be actuated out from actuation handle adapter guide cone 624, e.g., optic fiber distal end 101 may be actuated into actuation handle adapter housing 730. In one or more embodiments, optic fiber distal end 101 may be actuated out from actuation handle adapter housing 730, e.g., optic fiber distal end 101 may be actuated into actuation handle guide cone 735. Illustratively, actuation handle guide cone 735 may be configured to guide a portion of replaceable optic fiber 300 into actuation handle inner bore 740. In one or more embodiments, optic fiber distal end 101 may be actuated out from actuation handle guide cone 735, e.g., optic fiber distal end 101 may be actuated into actuation handle inner bore 740. Illustratively, optic fiber distal end 101 may be actuated out from actuation handle inner bore 740, e.g., optic fiber distal end 101 may be actuated into actuation handle distal chamber 745. In one or more embodiments, optic fiber distal end 101 may be actuated out from actuation handle distal chamber 745, e.g., optic fiber distal end 101 may be actuated into inner nosecone 930. Illustratively, optic fiber distal end 101 may be actuated out from inner nosecone 930, e.g., optic fiber distal end 101 may be actuated into housing tube 800. In one or more embodiments, a portion of replaceable optic fiber 300 may be actuated into actuation handle 700 wherein optic fiber distal end 101 may be adjacent to housing tube distal end 801. Illustratively, a portion of replaceable optic fiber 300 may be disposed within housing tube 800 wherein optic fiber distal end 101 may be adjacent to housing tube distal end 801.

In one or more embodiments, a portion of first connector 200 may be disposed within actuation handle adapter 600. Illustratively, first connector distal end 201 may be actuated into actuation handle adapter 600. In one or more embodiments, first connector distal end 201 may be actuated into actuation handle adapter proximal taper 614. Illustratively, first connector distal end 201 may be actuated out from actuation handle adapter proximal taper 614, e.g., first connector distal end 201 may be actuated into actuation handle adapter proximal chamber 613. In one or more embodiments, first connector distal end 201 may be actuated out from actuation handle adapter proximal chamber 613, e.g., first connector distal end 201 may be actuated into actuation handle adapter inner bore 623. Illustratively, a portion of first connector 200 may be temporarily fixed within actuation handle adapter 600. In one or more embodiments, canted coil spring 400 may be configured to temporarily fix a portion of first connector 200 within actuation handle adapter 600. Illustratively, as first connector distal end 201 is actuated into actuation handle adapter inner bore 623, canted coil spring 400 may interface with a portion of first connector 200, e.g., canted coil spring 400 may interface with temporary fixation channel 205. In one or more embodiments, an interface between canted coil spring 400 and temporary fixation channel 205 may be configured to temporarily fix a portion of first connector 200 within actuation handle adapter 600. Illustratively, a portion of first connector 200 may be temporarily fixed within actuation handle adapter 600, e.g., by a spring force or any suitable temporary fixation means.

In one or more embodiments, a compression of actuation structure 720 may be configured to extend inner nosecone housing 750 relative to actuation handle proximal end 702. Illustratively, an extension of inner nosecone housing 750 relative to actuation handle proximal end 702 may be configured to extend inner nosecone 930 relative to actuation handle proximal end 702. In one or more embodiments, an extension of inner nosecone 930 relative to actuation handle proximal end 702 may be configured to extend housing tube 800 relative to actuation handle proximal end 702. Illustratively, a compression of actuation structure 720 may be configured to extend housing tube 800 relative to actuation handle proximal end 702, e.g., a compression of actuation structure 720 may be configured to extend housing tube distal end 801. In one or more embodiments, an extension of housing tube 800 relative to actuation handle proximal end 702 may be configured to extend housing tube 800 relative to cable 850. Illustratively, cable 850 may be configured to resist an extension of housing tube 800 relative to cable 850, e.g., a portion of cable 850 fixed to a portion of housing tube 800 may apply a resistive force to a portion of housing tube 800. In one or more embodiments, an application a force to a portion of housing tube 800 may be configured to compress a portion of housing tube 800, e.g., an application of a force to a portion of housing tube 800 may be configured to compress first housing tube portion 820. Illustratively, a compression of a portion of housing tube 800 may be configured to cause housing tube 800 to gradually curve. In one or more embodiments, a gradual curving of housing tube 800 may be configured to gradually curve a portion of replaceable optic fiber 300, e.g., a gradual curving of housing tube 800 may be configured to curve a portion of optic fiber 100 disposed within housing tube 800. Illustratively, a compression of actuation structure 720 may be configured to gradually curve a portion of optic fiber 100.

In one or more embodiments, a decompression of actuation structure 720 may be configured to retract inner nosecone housing 750 relative to actuation handle proximal end 702. Illustratively, a retraction of inner nosecone housing 750 relative to actuation handle proximal end 702 may be configured to retract inner nosecone 930 relative to actuation handle proximal end 702. In one or more embodiments, a retraction of inner nosecone 930 relative to actuation handle proximal end 702 may be configured to retract housing tube 800 relative to actuation handle proximal end 702. Illustratively, a decompression of actuation structure 720 may be configured to retract housing tube 800 relative to actuation handle proximal end 702, e.g., a decompression of actuation structure 720 may be configured to retract housing tube distal end 801. In one or more embodiments, a refraction of housing tube 800 relative to actuation handle proximal end 702 may be configured to retract housing tube 800 relative to cable 850. Illustratively, cable 850 may be configured to facilitate a retraction of housing tube 800 relative to cable 850, e.g., a portion of cable 850 fixed to a portion of housing tube 800 may reduce a resistive force applied to a portion of housing tube 800. In one or more embodiments, a reduction of a force applied to a portion of housing tube 800 may be configured to decompress a portion of housing tube 800, e.g., a reduction of a force applied to a portion of housing tube 800 may be configured to decompress first housing tube portion 820. Illustratively, a decompression of a portion of housing tube 800 may be configured to cause housing tube 800 to gradually straighten. In one or more embodiments, a gradual straightening of housing tube 800 may be configured to gradually straighten a portion of replaceable optic fiber 300, e.g., a gradual straightening of housing tube 800 may be configured to straighten a portion of optic fiber 100 disposed within housing tube 800. Illustratively, a decompression of actuation structure 720 may be configured to gradually straighten a portion of optic fiber 100.

Figure 10A:
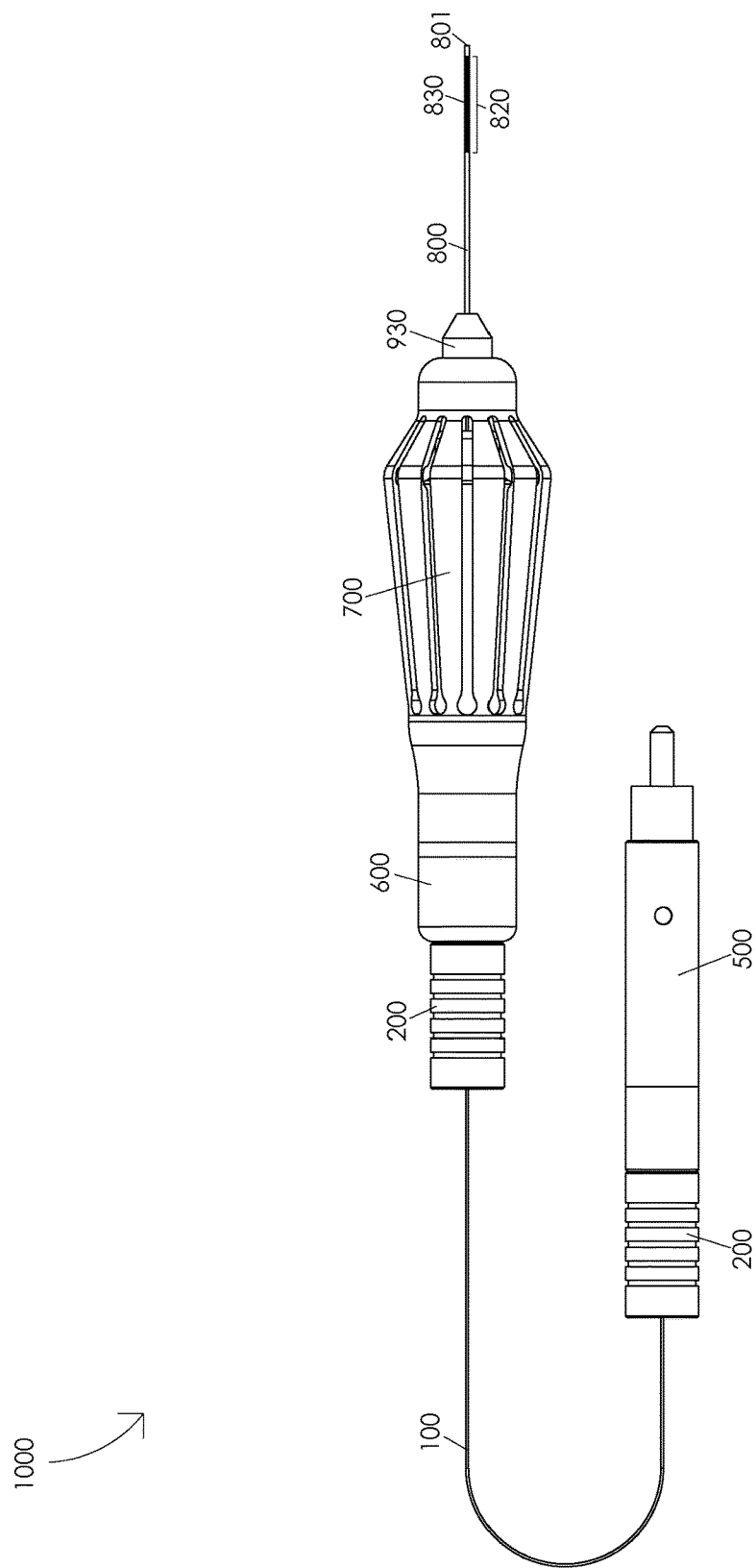
FIGS. 10A, 10B, 10C, 10D, and 10E illustrate a gradual curving of an optic fiber.

FIGS. 10A, 10B, 10C, 10D, and 10E illustrate a gradual curving of an optic fiber 100. FIG. 10A illustrates a straight optic fiber 1000. In one or more embodiments, optic fiber 100 may comprise a straight optic fiber 1000, e.g., when inner nosecone 930 is fully refracted relative to actuation handle proximal end 702. Illustratively, optic fiber 100 may comprise a straight optic fiber 1000, e.g., when actuation structure 720 is fully decompressed. In one or more embodiments, optic fiber 100 may comprise a straight optic fiber 1000, e.g., when first housing tube portion 820 is fully decompressed. Illustratively, a line tangent to optic fiber distal end 101 may be parallel to a line tangent to housing tube proximal end 802, e.g., when optic fiber 100 comprises a straight optic fiber 1000.

Figure 10B:
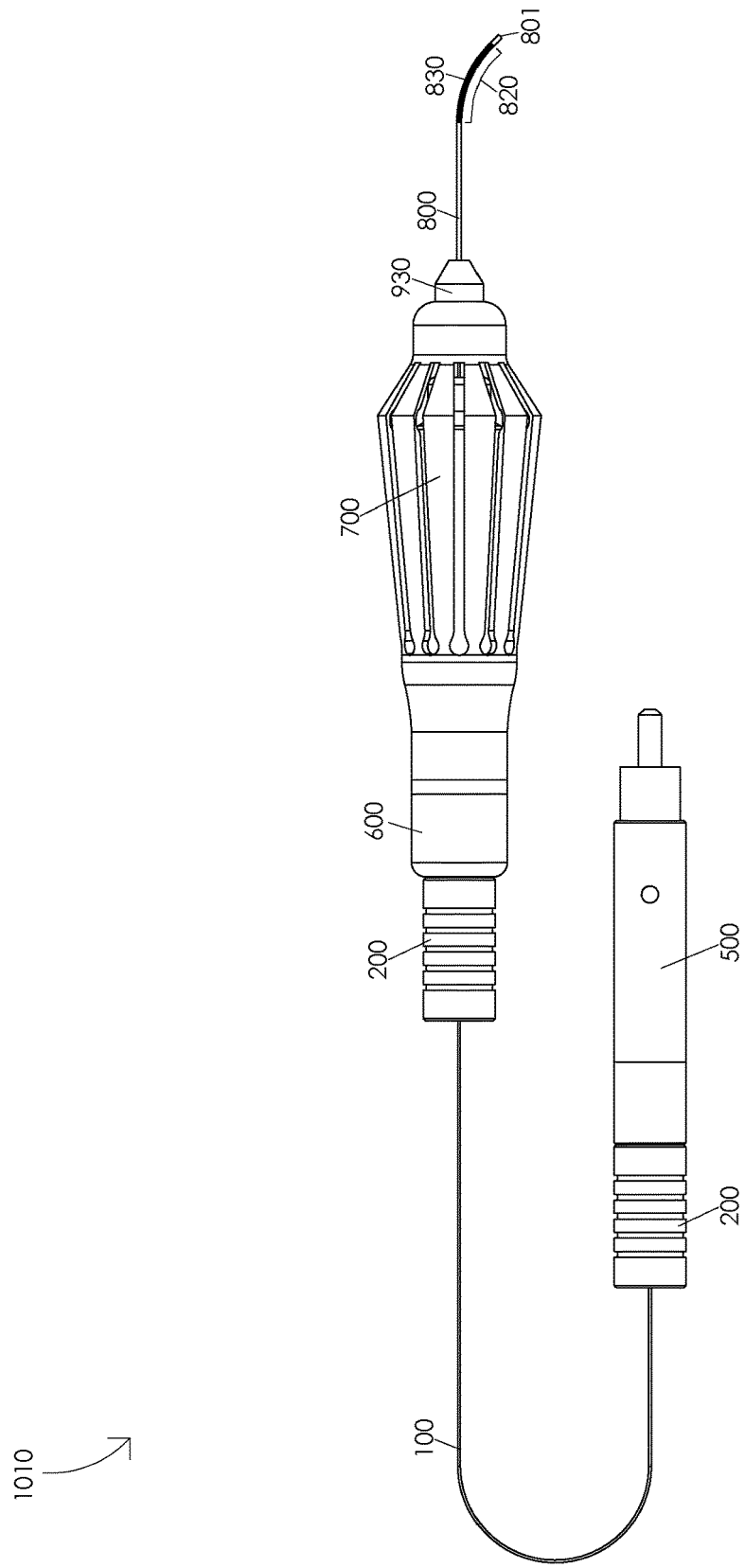

FIG. 10B illustrates an optic fiber in a first curved position 1010. In one or more embodiments, a compression of actuation structure 720 may be configured to gradually curve optic fiber 100 from a straight optic fiber 1000 to an optic fiber in a first curved position 1010. Illustratively, a compression of actuation structure 720 may be configured to extend housing tube 800 relative to actuation handle proximal end 702. In one or more embodiments, an extension of housing tube 800 relative to actuation handle proximal end 702 may be configured to extend housing tube 800 relative to cable 850. Illustratively, a portion of cable 850, e.g., a portion of cable 850 fixed to a portion of housing tube 800, may be configured to resist an extension of housing tube 800 relative to cable 850. In one or more embodiments, cable 850 may be configured to apply a force to a portion of housing tube 800, e.g., cable 850 may be configured to apply a force to a portion of housing tube 800 to resist an extension of housing tube 800 relative to cable 850. Illustratively, an application of a force to a portion of housing tube 800 may be configured to compress a portion of housing tube 800, e.g., an application of a force to a portion of housing tube 800 may be configured to compress first housing tube portion 820. In one or more embodiments, a compression of a portion of housing tube 800 may be configured to gradually curve housing tube 800. Illustratively, a gradual curving of housing tube 800 may be configured to gradually curve optic fiber 100, e.g., from a straight optic fiber 1000 to an optic fiber in a first curved position 1010. In one or more embodiments, a line tangent to optic fiber distal end 101 may intersect a line tangent to housing tube proximal end 802 at a first angle, e.g., when optic fiber 100 comprises an optic fiber in a first curved position 1010. Illustratively, the first angle may comprise any angle greater than zero degrees, e.g., the first angle may comprise a 45 degree angle.

Figure 10C:
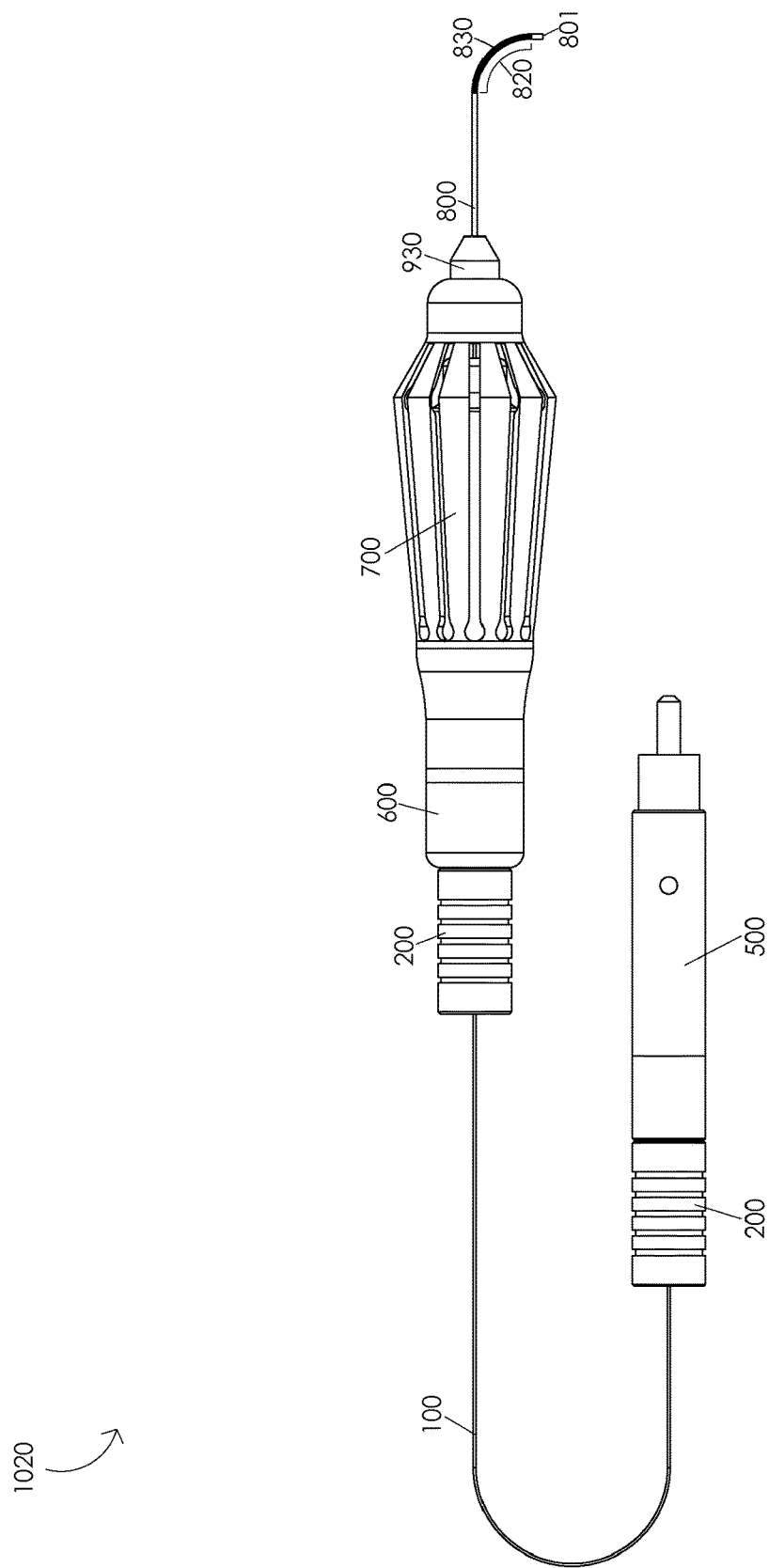

FIG. 10C illustrates an optic fiber in a second curved position 1020. In one or more embodiments, a compression of actuation structure 720 may be configured to gradually curve optic fiber 100 from an optic fiber in a first curved position 1010 to an optic fiber in a second curved position 1020. Illustratively, a compression of actuation structure 720 may be configured to extend housing tube 800 relative to actuation handle proximal end 702. In one or more embodiments, an extension of housing tube 800 relative to actuation handle proximal end 702 may be configured to extend housing tube 800 relative to cable 850. Illustratively, a portion of cable 850, e.g., a portion of cable 850 fixed to a portion of housing tube 800, may be configured to resist an extension of housing tube 800 relative to cable 850. In one or more embodiments, cable 850 may be configured to apply a force to a portion of housing tube 800, e.g., cable 850 may be configured to apply a force to a portion of housing tube 800 to resist an extension of housing tube 800 relative to cable 850. Illustratively, an application of a force to a portion of housing tube 800 may be configured to compress a portion of housing tube 800, e.g., an application of a force to a portion of housing tube 800 may be configured to compress first housing tube portion 820. In one or more embodiments, a compression of a portion of housing tube 800 may be configured to gradually curve housing tube 800. Illustratively, a gradual curving of housing tube 800 may be configured to gradually curve optic fiber 100, e.g., from an optic fiber in a first curved position 1010 to an optic fiber in a second curved position 1020. In one or more embodiments, a line tangent to optic fiber distal end 101 may intersect a line tangent to housing tube proximal end 802 at a second angle, e.g., when optic fiber 100 comprises an optic fiber in a second curved position 1020. Illustratively, the second angle may comprise any angle greater than the first angle, e.g., the second angle may comprise a 90 degree angle.

Figure 10D:
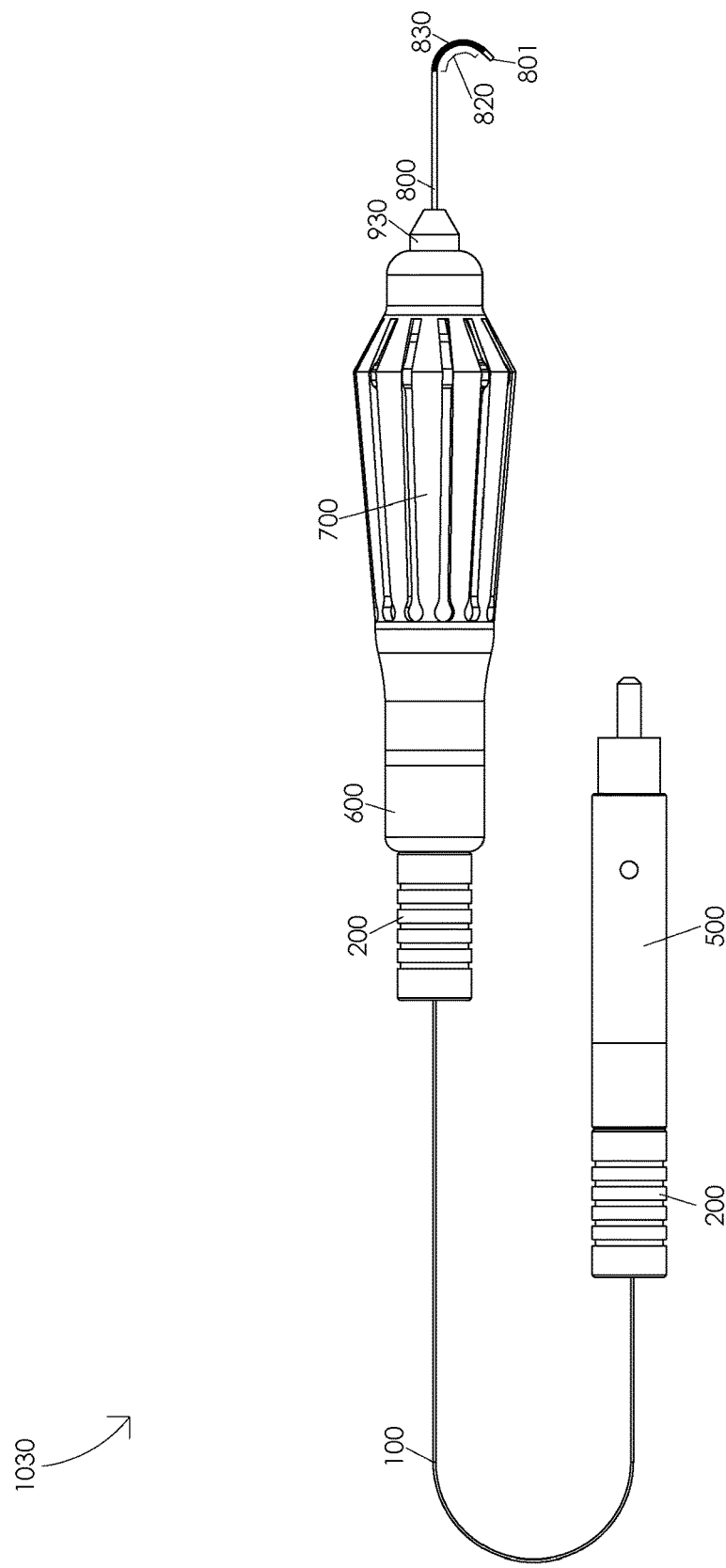

FIG. 10D illustrates an optic fiber in a third curved position 1030. In one or more embodiments, a compression of actuation structure 720 may be configured to gradually curve optic fiber 100 from an optic fiber in a second curved position 1020 to an optic fiber in a third curved position 1030. Illustratively, a compression of actuation structure 720 may be configured to extend housing tube 800 relative to actuation handle proximal end 702. In one or more embodiments, an extension of housing tube 800 relative to actuation handle proximal end 702 may be configured to extend housing tube 800 relative to cable 850. Illustratively, a portion of cable 850, e.g., a portion of cable 850 fixed to a portion of housing tube 800, may be configured to resist an extension of housing tube 800 relative to cable 850. In one or more embodiments, cable 850 may be configured to apply a force to a portion of housing tube 800, e.g., cable 850 may be configured to apply a force to a portion of housing tube 800 to resist an extension of housing tube 800 relative to cable 850. Illustratively, an application of a force to a portion of housing tube 800 may be configured to compress a portion of housing tube 800, e.g., an application of a force to a portion of housing tube 800 may be configured to compress first housing tube portion 820. In one or more embodiments, a compression of a portion of housing tube 800 may be configured to gradually curve housing tube 800. Illustratively, a gradual curving of housing tube 800 may be configured to gradually curve optic fiber 100, e.g., from an optic fiber in a second curved position 1020 to an optic fiber in a third curved position 1030. In one or more embodiments, a line tangent to optic fiber distal end 101 may intersect a line tangent to housing tube proximal end 802 at a third angle, e.g., when optic fiber 100 comprises an optic fiber in a third curved position 1030. Illustratively, the third angle may comprise any angle greater than the second angle, e.g., the third angle may comprise a 135 degree angle.

Figure 10E:
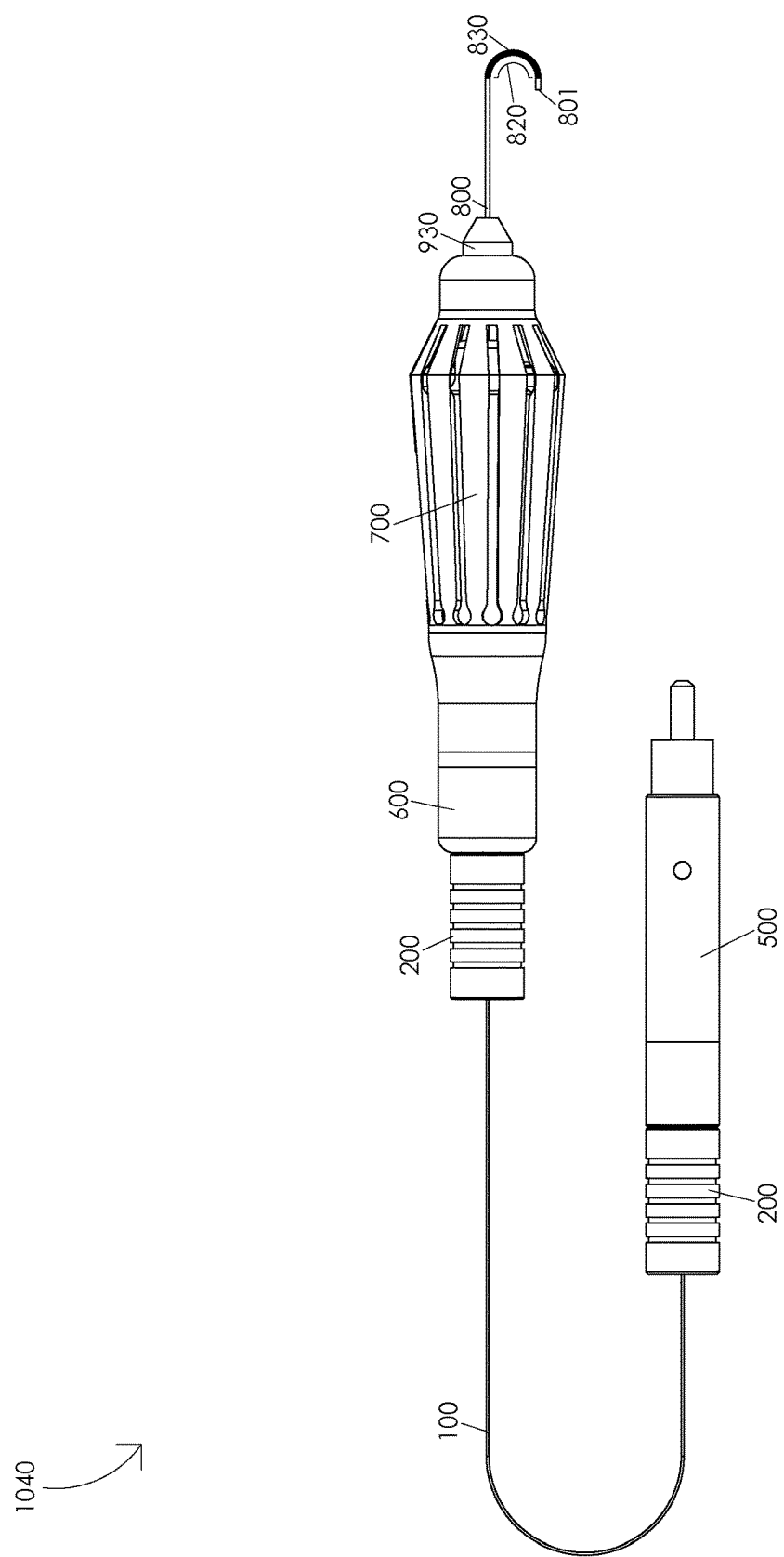

FIG. 10E illustrates an optic fiber in a fourth curved position 1040. In one or more embodiments, a compression of actuation structure 720 may be configured to gradually curve optic fiber 100 from an optic fiber in a third curved position 1030 to an optic fiber in a fourth curved position 1040. Illustratively, a compression of actuation structure 720 may be configured to extend housing tube 800 relative to actuation handle proximal end 702. In one or more embodiments, an extension of housing tube 800 relative to actuation handle proximal end 702 may be configured to extend housing tube 800 relative to cable 850. Illustratively, a portion of cable 850, e.g., a portion of cable 850 fixed to a portion of housing tube 800, may be configured to resist an extension of housing tube 800 relative to cable 850. In one or more embodiments, cable 850 may be configured to apply a force to a portion of housing tube 800, e.g., cable 850 may be configured to apply a force to a portion of housing tube 800 to resist an extension of housing tube 800 relative to cable 850. Illustratively, an application of a force to a portion of housing tube 800 may be configured to compress a portion of housing tube 800, e.g., an application of a force to a portion of housing tube 800 may be configured to compress first housing tube portion 820. In one or more embodiments, a compression of a portion of housing tube 800 may be configured to gradually curve housing tube 800. Illustratively, a gradual curving of housing tube 800 may be configured to gradually curve optic fiber 100, e.g., from an optic fiber in a third curved position 1030 to an optic fiber in a fourth curved position 1040. In one or more embodiments, a line tangent to optic fiber distal end 101 may be parallel to a line tangent to housing tube proximal end 802, e.g., when optic fiber 100 comprises an optic fiber in a fourth curved position 1040.

Figure 11A:
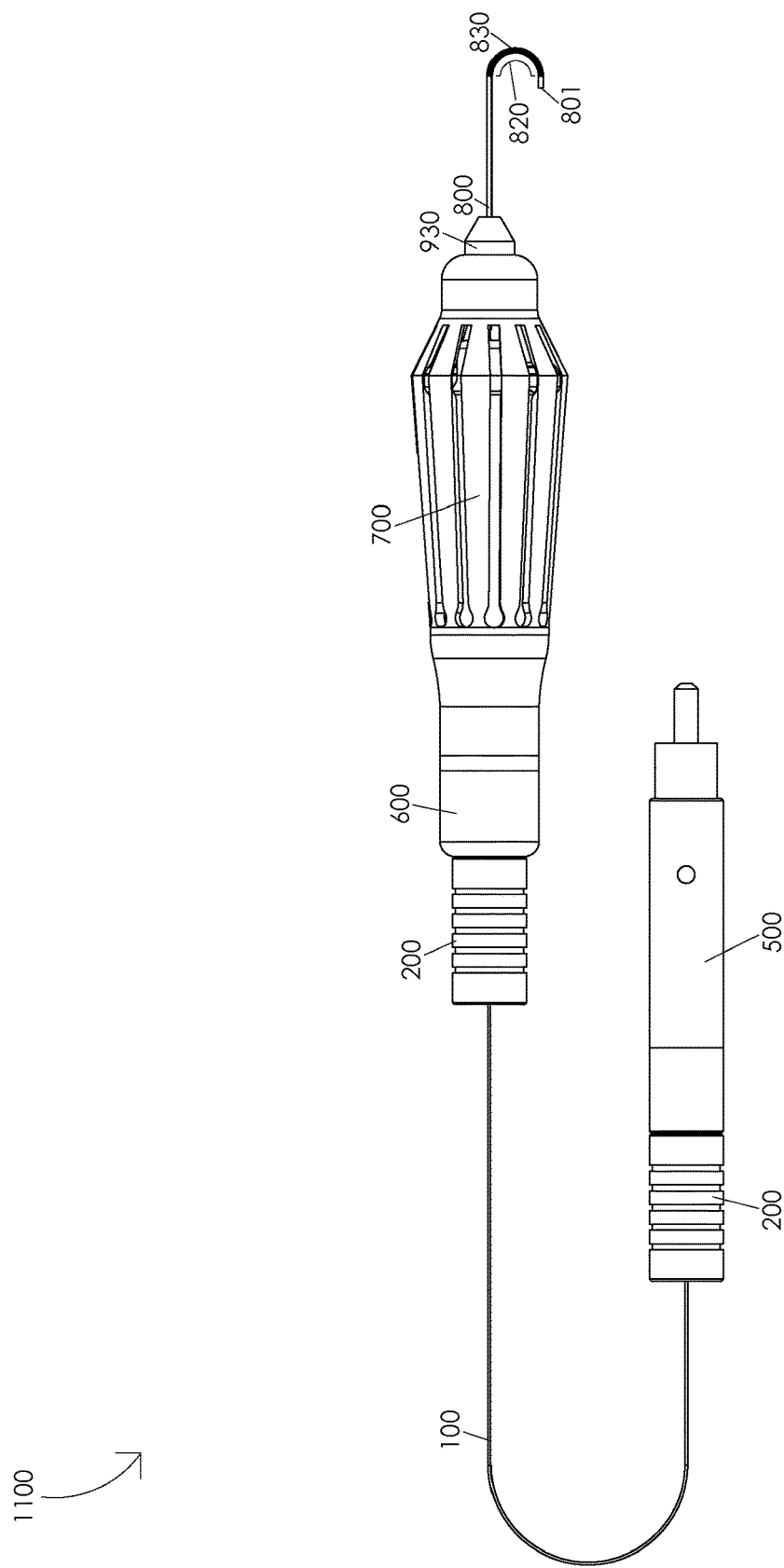
FIGS. 11A, 11B, 11C, 11D, and 11E illustrate a gradual straightening of an optic fiber.

FIGS. 11A, 11B, 11C, 11D, and 11E illustrate a gradual straightening of an optic fiber 100. FIG. 11A illustrates a fully curved optic fiber 1100. In one or more embodiments, optic fiber 100 may comprise a fully curved optic fiber 1100, e.g., when inner nosecone 930 is fully extended relative to actuation handle proximal end 702. Illustratively, optic fiber 100 may comprise a fully curved optic fiber 1100, e.g., when actuation structure 720 is fully compressed. In one or more embodiments, optic fiber 100 may comprise a fully curved optic fiber 1100, e.g., when first housing tube portion 820 is fully compressed. Illustratively, a line tangent to optic fiber distal end 101 may be parallel to a line tangent to housing tube proximal end 802, e.g., when optic fiber 100 comprises a fully curved optic fiber 1100.

Figure 11B:
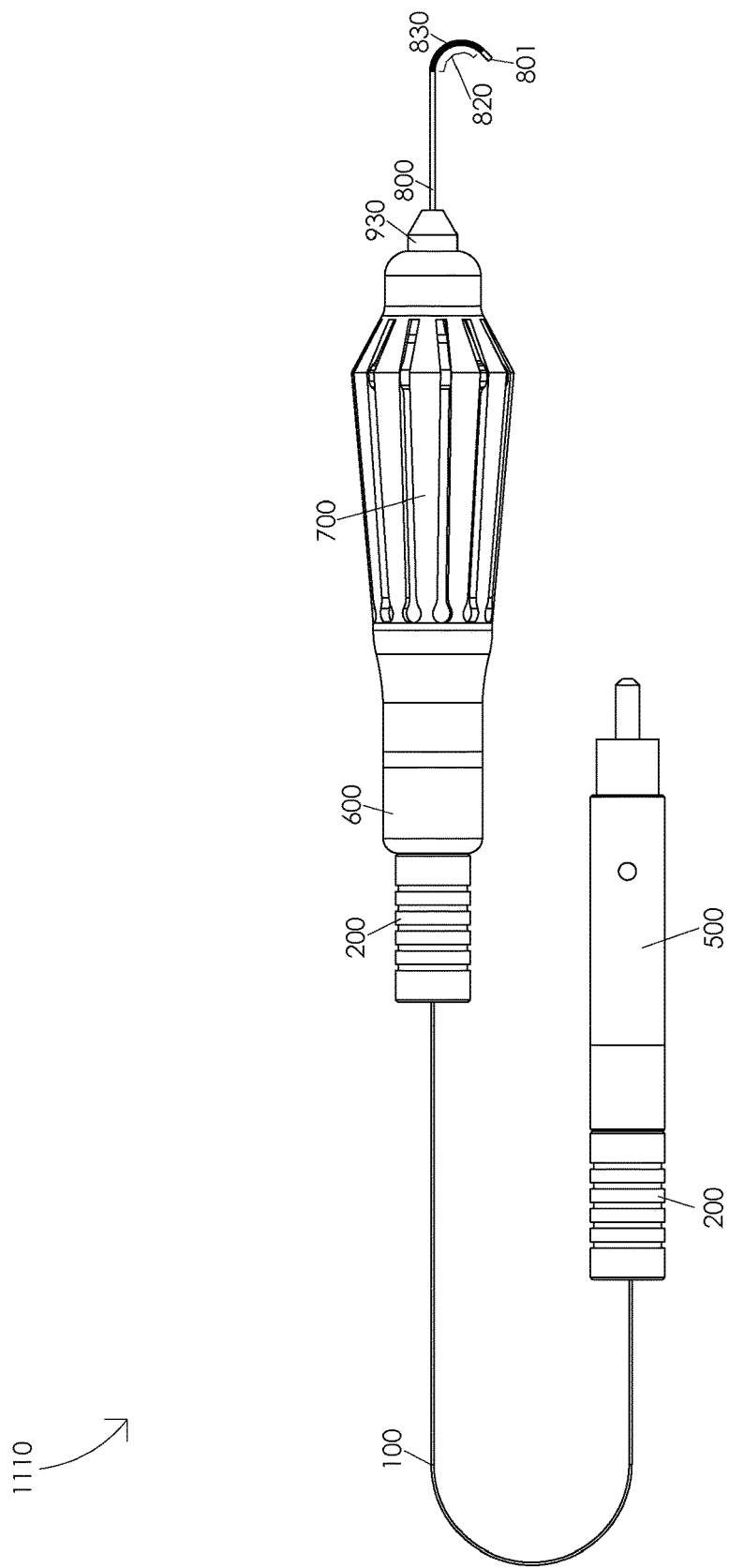

FIG. 11B illustrates an optic fiber in a first partially straightened position 1110. In one or more embodiments, a decompression of actuation structure 720 may be configured to gradually straighten optic fiber 100 from a fully curved optic fiber 1100 to an optic fiber in a first partially straightened position 1110. Illustratively, a decompression of actuation structure 720 may be configured to retract housing tube 800 relative to actuation handle proximal end 702. In one or more embodiments, a retraction of housing tube 800 relative to actuation handle proximal end 702 may be configured to retract housing tube 800 relative to cable 850. Illustratively, a portion of cable 850, e.g., a portion of cable 850 fixed to a portion of housing tube 800, may be configured to facilitate a refraction of housing tube 800 relative to cable 850. In one or more embodiments, a retraction of housing tube 800 relative to cable 850 may be configured to reduce a force applied to a portion of housing tube 800. Illustratively, a reduction of a force applied to a portion of housing tube 800 may be configured to decompress a portion of housing tube 800, e.g., a reduction of a force applied to a portion of housing tube 800 may be configured to decompress first housing tube portion 820. In one or more embodiments, a decompression of a portion of housing tube 800 may be configured to gradually straighten housing tube 800. Illustratively, a gradual straightening of housing tube 800 may be configured to gradually straighten optic fiber 100, e.g., from a fully curved optic fiber 1100 to an optic fiber in a first partially straightened position 1110. In one or more embodiments, a line tangent to optic fiber distal end 101 may intersect a line tangent to housing tube proximal end 802 at a first partially straightened angle, e.g., when optic fiber 100 comprises an optic fiber in a first partially straightened position 1110. Illustratively, the first partially straightened angle may comprise any angle less than 180 degrees, e.g., the first partially straightened angle may comprise a 135 degree angle.

Figure 11C:
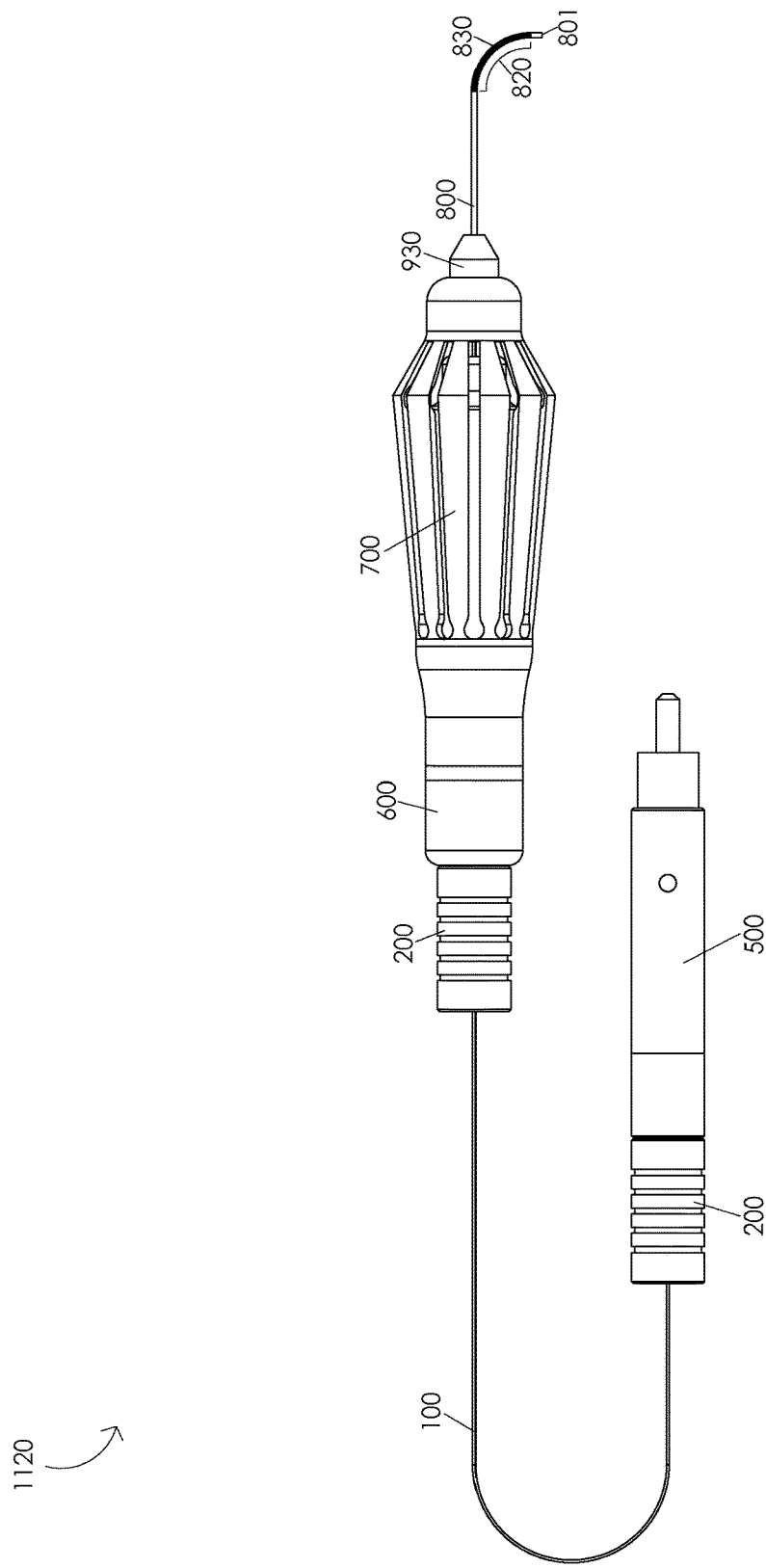

FIG. 11C illustrates an optic fiber in a second partially straightened position 1120. In one or more embodiments, a decompression of actuation structure 720 may be configured to gradually straighten optic fiber 100 from an optic fiber in a first partially straightened position 1110 to an optic fiber in a second partially straightened position 1120. Illustratively, a decompression of actuation structure 720 may be configured to retract housing tube 800 relative to actuation handle proximal end 702. In one or more embodiments, a refraction of housing tube 800 relative to actuation handle proximal end 702 may be configured to retract housing tube 800 relative to cable 850. Illustratively, a portion of cable 850, e.g., a portion of cable 850 fixed to a portion of housing tube 800, may be configured to facilitate a retraction of housing tube 800 relative to cable 850. In one or more embodiments, a retraction of housing tube 800 relative to cable 850 may be configured to reduce a force applied to a portion of housing tube 800. Illustratively, a reduction of a force applied to a portion of housing tube 800 may be configured to decompress a portion of housing tube 800, e.g., a reduction of a force applied to a portion of housing tube 800 may be configured to decompress first housing tube portion 820. In one or more embodiments, a decompression of a portion of housing tube 800 may be configured to gradually straighten housing tube 800. Illustratively, a gradual straightening of housing tube 800 may be configured to gradually straighten optic fiber 100, e.g., from an optic fiber in a first partially straightened position 1110 to an optic fiber in a second partially straightened position 1120. In one or more embodiments, a line tangent to optic fiber distal end 101 may intersect a line tangent to housing tube proximal end 802 at a second partially straightened angle, e.g., when optic fiber 100 comprises an optic fiber in a second partially straightened position 1120. Illustratively, the second partially straightened angle may comprise any angle less than the first partially straightened angle, e.g., the second partially straightened angle may comprise a 90 degree angle.

Figure 11D:
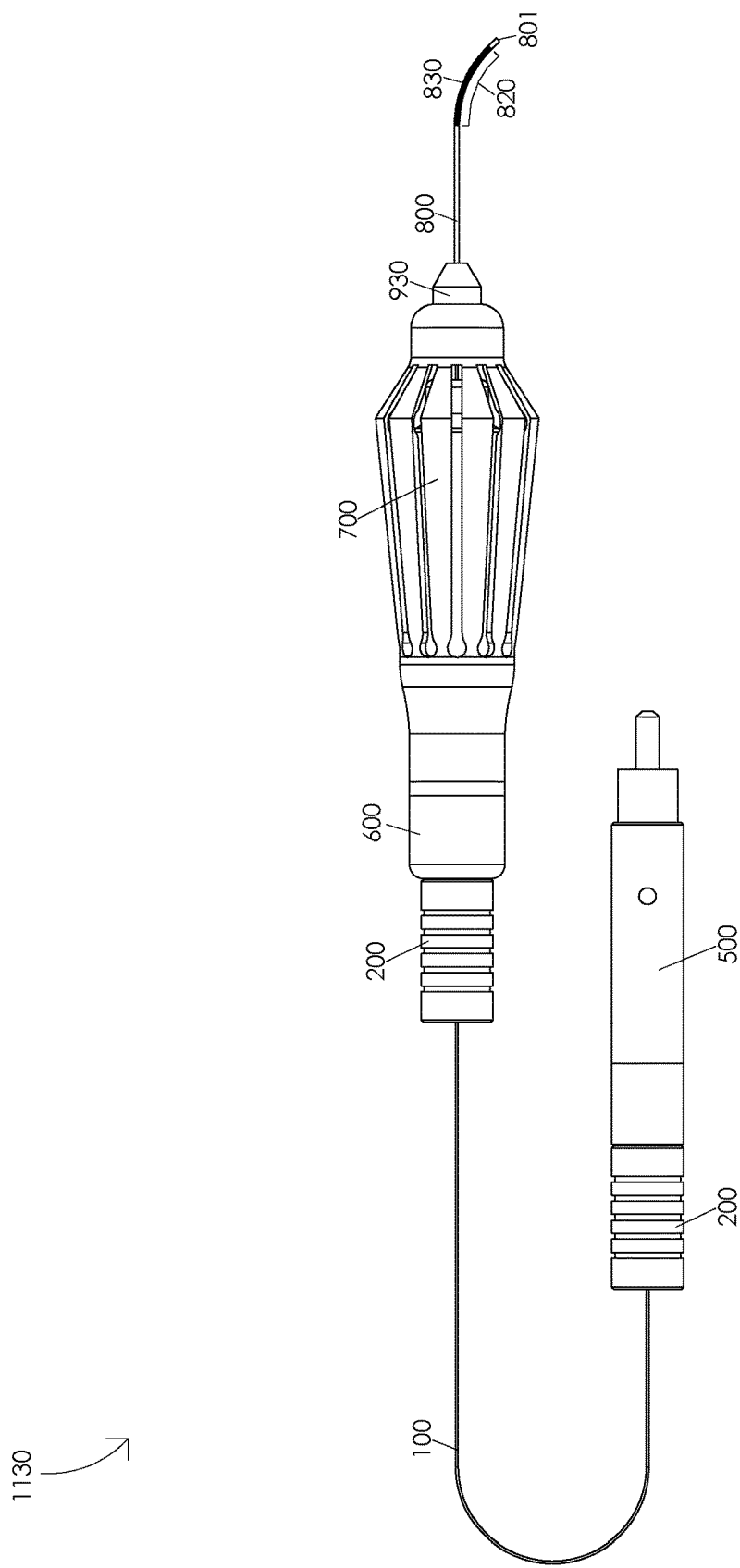

FIG. 11D illustrates an optic fiber in a third partially straightened position 1130. In one or more embodiments, a decompression of actuation structure 720 may be configured to gradually straighten optic fiber 100 from an optic fiber in a second partially straightened position 1120 to an optic fiber in a third partially straightened position 1130. Illustratively, a decompression of actuation structure 720 may be configured to retract housing tube 800 relative to actuation handle proximal end 702. In one or more embodiments, a refraction of housing tube 800 relative to actuation handle proximal end 702 may be configured to retract housing tube 800 relative to cable 850. Illustratively, a portion of cable 850, e.g., a portion of cable 850 fixed to a portion of housing tube 800, may be configured to facilitate a retraction of housing tube 800 relative to cable 850. In one or more embodiments, a retraction of housing tube 800 relative to cable 850 may be configured to reduce a force applied to a portion of housing tube 800. Illustratively, a reduction of a force applied to a portion of housing tube 800 may be configured to decompress a portion of housing tube 800, e.g., a reduction of a force applied to a portion of housing tube 800 may be configured to decompress first housing tube portion 820. In one or more embodiments, a decompression of a portion of housing tube 800 may be configured to gradually straighten housing tube 800. Illustratively, a gradual straightening of housing tube 800 may be configured to gradually straighten optic fiber 100, e.g., from an optic fiber in a second partially straightened position 1120 to an optic fiber in a third partially straightened position 1130. In one or more embodiments, a line tangent to optic fiber distal end 101 may intersect a line tangent to housing tube proximal end 802 at a third partially straightened angle, e.g., when optic fiber 100 comprises an optic fiber in a third partially straightened position 1130. Illustratively, the third partially straightened angle may comprise any angle less than the second partially straightened angle, e.g., the third partially straightened angle may comprise a 45 degree angle.

Figure 11E:
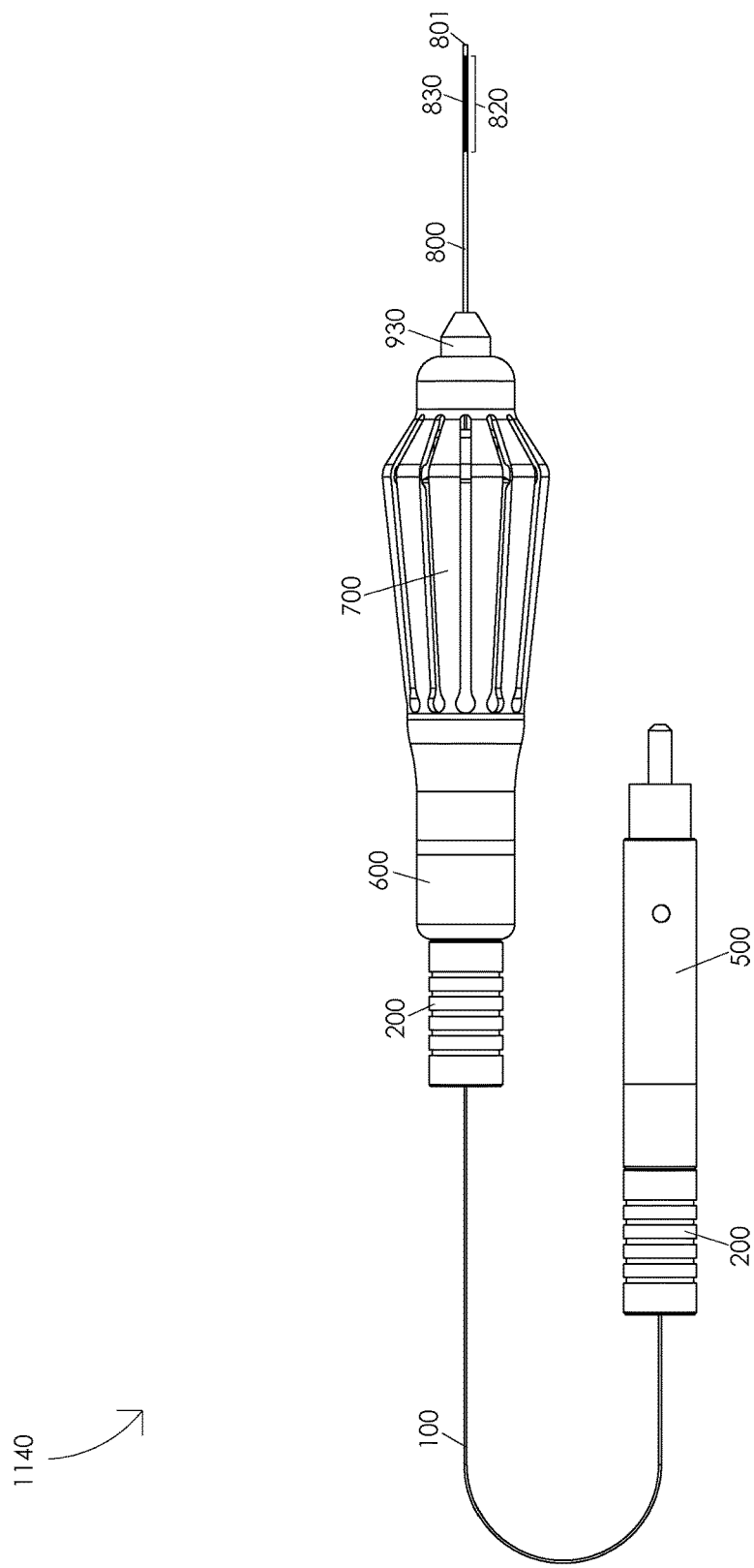

FIG. 11E illustrates an optic fiber in a fully straightened position 1140. In one or more embodiments, a decompression of actuation structure 720 may be configured to gradually straighten optic fiber 100 from an optic fiber in a third partially straightened position 1130 to an optic fiber in a fully straightened position 1140. Illustratively, a decompression of actuation structure 720 may be configured to retract housing tube 800 relative to actuation handle proximal end 702. In one or more embodiments, a retraction of housing tube 800 relative to actuation handle proximal end 702 may be configured to retract housing tube 800 relative to cable 850. Illustratively, a portion of cable 850, e.g., a portion of cable 850 fixed to a portion of housing tube 800, may be configured to facilitate a retraction of housing tube 800 relative to cable 850. In one or more embodiments, a retraction of housing tube 800 relative to cable 850 may be configured to reduce a force applied to a portion of housing tube 800. Illustratively, a reduction of a force applied to a portion of housing tube 800 may be configured to decompress a portion of housing tube 800, e.g., a reduction of a force applied to a portion of housing tube 800 may be configured to decompress first housing tube portion 820. In one or more embodiments, a decompression of a portion of housing tube 800 may be configured to gradually straighten housing tube 800. Illustratively, a gradual straightening of housing tube 800 may be configured to gradually straighten optic fiber 100, e.g., from an optic fiber in a third partially straightened position 1130 to an optic fiber in a fully straightened position 1140. In one or more embodiments, a line tangent to optic fiber distal end 101 may be parallel to a line tangent to housing tube proximal end 802, e.g., when optic fiber 100 comprises an optic fiber in a fully straightened position 1140.

Illustratively, a surgeon may aim optic fiber distal end 101 at any of a plurality of targets within an eye, e.g., to perform a photocoagulation procedure, to illuminate a surgical target site, etc. In one or more embodiments, a surgeon may aim optic fiber distal end 101 at any target within a particular transverse plane of the inner eye by, e.g., rotating actuation handle 700 to orient housing tube 800 in an orientation configured to cause a curvature of housing tube 800 within the particular transverse plane of the inner eye and varying an amount of compression of actuation structure 720. Illustratively, a surgeon may aim optic fiber distal end 101 at any target within a particular sagittal plane of the inner eye by, e.g., rotating actuation handle 700 to orient housing tube 800 in an orientation configured to cause a curvature of housing tube 800 within the particular sagittal plane of the inner eye and varying an amount of compression of actuation structure 720. In one or more embodiments, a surgeon may aim optic fiber distal end 101 at any target within a particular frontal plane of the inner eye by, e.g., varying an amount of compression of actuation structure 720 to orient a line tangent to optic fiber distal end 101 wherein the line tangent to optic fiber distal end 101 is within the particular frontal plane of the inner eye and rotating actuation handle 700. Illustratively, a surgeon may aim optic fiber distal end 101 at any target located outside of the particular transverse plane, the particular sagittal plane, and the particular frontal plane of the inner eye, e.g., by varying a rotational orientation of actuation handle 700 and varying an amount of compression of actuation structure 720. In one or more embodiments, a surgeon may aim optic fiber distal end 101 at any target of a plurality of targets within an eye, e.g., without increasing a length of a portion of a steerable laser probe with a replaceable optic fiber within the eye. Illustratively, a surgeon may aim optic fiber distal end 101 at any target of a plurality of targets within an eye, e.g., without decreasing a length of a portion of a steerable laser probe with a replaceable optic fiber within the eye.

In one or more embodiments, replaceable optic fiber 300 may comprise a single use, disposable medical device, e.g., replaceable optic fiber 300 may be sold as a sterile product. Illustratively, replaceable optic fiber 300 may be sold as a sterile product in a hermetically sealed package, e.g., sterilized by ethylene oxide sterilization. In one or more embodiments, replaceable optic fiber 300 may be configured for use in a single surgical procedure, e.g., a new replaceable optic fiber 300 may be required for each surgical procedure. Illustratively, machine adapter 500 may comprise a reusable medical device, e.g., machine adapter 500 may be sold as a non-sterile product. In one or more embodiments, actuation handle adapter 600 may comprise a reusable medical device, e.g., actuation handle adapter 600 may be sold as a non-sterile product. Illustratively, actuation handle 700, inner nosecone 930, and housing tube 800 may comprise a single reusable medical device, e.g., actuation handle 700, inner nosecone 930, and housing tube 800 may be sold as a non-sterile product.

In one or more embodiments, machine adapter 500, actuation handle adapter 600, actuation handle 700, inner nosecone 930, and housing tube 800 may be sterilized a first time, e.g., by a medical autoclave. Illustratively, a first replaceable fiber 300 hermetically sealed package may be opened to prepare for a first surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into actuation handle adapter 600, e.g., first connector 200 may be temporarily fixed within actuation handle adapter 600. Illustratively, a surgeon may then perform a first surgical procedure, e.g. a surgeon may perform a photocoagulation surgical procedure. After performing the first surgical procedure, the first replaceable optic fiber 300 may be discarded, e.g., second connector 200 may be removed from machine adapter 500, first connector 200 may be removed from actuation handle adapter 600, and the first replaceable optic fiber 300 may be placed in a medical waste disposal bin. In one or more embodiments, machine adapter 500, actuation handle adapter 600, actuation handle 700, inner nosecone 930, and housing tube 800 may be sterilized a second time, e.g., by a medical autoclave. Illustratively, a second replaceable fiber 300 hermetically sealed package may be opened to prepare for a second surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into actuation handle adapter 600, e.g., first connector 200 may be temporarily fixed within actuation handle adapter 600. Illustratively, a surgeon may then perform a second surgical procedure, e.g. a surgeon may perform a photocoagulation surgical procedure. After performing the second surgical procedure, the second replaceable optic fiber 300 may be discarded, e.g., second connector 200 may be removed from machine adapter 500, first connector 200 may be removed from actuation handle adapter 600, and the second replaceable optic fiber 300 may be placed in a medical waste disposal bin. In one or more embodiments, machine adapter 500, actuation handle adapter 600, actuation handle 700, inner nosecone 930, and housing tube 800 may be sterilized a third time, e.g., by a medical autoclave. Illustratively, a third replaceable fiber 300 hermetically sealed package may be opened to prepare for a third surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into actuation handle adapter 600, e.g., first connector 200 may be temporarily fixed within actuation handle adapter 600. Illustratively, a surgeon may then perform a third surgical procedure, e.g. a surgeon may perform a photocoagulation surgical procedure. After performing the third surgical procedure, the third replaceable optic fiber 300 may be discarded, e.g., second connector 200 may be removed from machine adapter 500, first connector 200 may be removed from actuation handle adapter 600, and the third replaceable optic fiber 300 may be placed in a medical waste disposal bin.

Figure 12A:
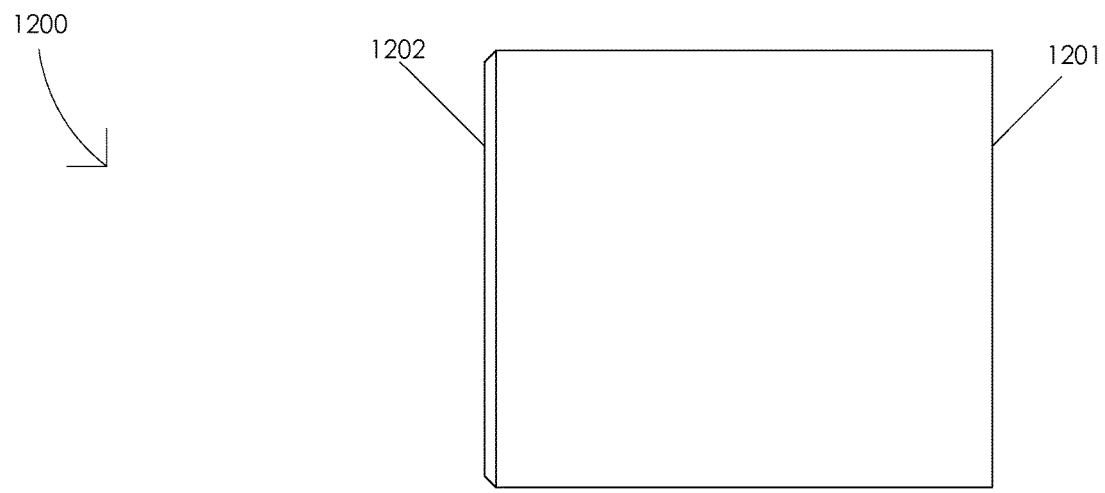
FIGS. 12A and 12B are schematic diagrams illustrating a handle adapter.
Figure 12B:
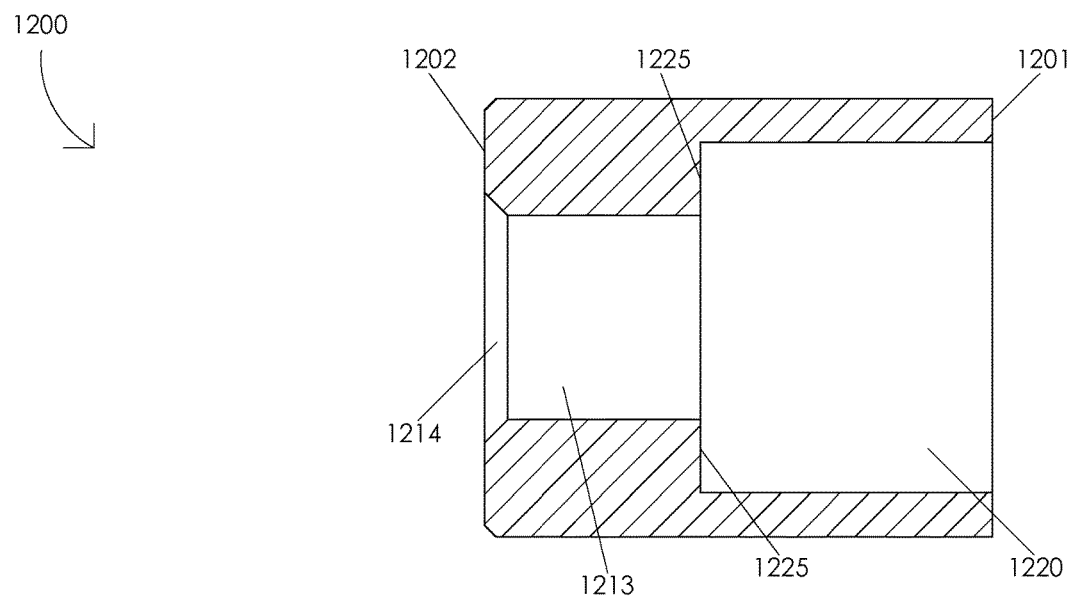

FIGS. 12A and 12B are schematic diagrams illustrating a handle adapter 1200. FIG. 12A illustrates a top view of handle adapter 1200. Illustratively, handle adapter 1200 may comprise a handle adapter distal end 1201 and a handle adapter proximal end 1202. FIG. 12B illustrates a cross-sectional view of handle adapter 1200. In one or more embodiments, handle adapter 1200 may comprise a handle adapter taper 1214, a handle adapter chamber 1213, a handle proximal end housing 1220, and a handle interface 1225. Handle adapter 1200 may be manufactured from any suitable material, e.g., polymers, metals, metal alloys, etc., or from any combination of suitable materials. In one or more embodiments, handle adapter 1200 may be manufactured from a material suitable for sterilization by a medical autoclave. Illustratively, handle adapter 1200 may be manufactured from a material, e.g., Nylon, titanium, stainless steel, etc., configured to withstand exposure to temperatures, pressures, and ambient conditions present in a medical autoclave without degradation. For example, handle adapter 1200 may be configured to function normally after exposure in a temperature 250° F. for 15 minutes at an atmospheric pressure of 15 psi. In one or more embodiments, handle adapter 1200 may be configured to be used in a surgical procedure and then sterilized by a medical autoclave at least three times. Illustratively, handle adapter 1200 may be configured to be used in a surgical procedure and then sterilized by a medical autoclave more than three times. In one or more embodiments, handle adapter 1200 may be sterilized in a medical autoclave and then handle adapter 1200 may be used in a first surgical procedure. Illustratively, handle adapter 1200 may be sterilized in a medical autoclave after use in the first surgical procedure and then handle adapter 1200 may be used in a second surgical procedure. In one or more embodiments, handle adapter 1200 may be sterilized in a medical autoclave after use in the second surgical procedure and then handle adapter 1200 may be used in a third surgical procedure.

FIGS. 13A and 13B are schematic diagrams illustrating a handle 1300. FIG. 13A illustrates a top view of handle 1300. Illustratively, handle 1300 may comprise a handle distal end 1301, a handle proximal end 1302, a handle grip 1320, and a handle adapter interface 1325. FIG. 13B illustrates a cross-sectional view of handle 1300. In one or more embodiments, handle 1300 may comprise a canted coil spring housing 1350, a handle proximal chamber 1330, a handle taper 1335, a handle inner bore 1340, a handle guide cone 1345, and an optic fiber distal end guide 1360. Handle 1300 may be manufactured from any suitable material, e.g., polymers, metals, metal alloys, etc., or from any combination of suitable materials. In one or more embodiments, handle 1300 may be manufactured from a material suitable for sterilization by a medical autoclave. Illustratively, handle 1300 may be manufactured from a material, e.g., Nylon, titanium, stainless steel, etc., configured to withstand exposure to temperatures, pressures, and ambient conditions present in a medical autoclave without degradation. For example, handle 1300 may be configured to function normally after exposure in a temperature 250° F. for 15 minutes at an atmospheric pressure of 15 psi. In one or more embodiments, handle 1300 may be configured to be used in a surgical procedure and then sterilized by a medical autoclave at least three times. Illustratively, handle 1300 may be configured to be used in a surgical procedure and then sterilized by a medical autoclave more than three times. In one or more embodiments, handle 1300 may be sterilized in a medical autoclave and then handle 1300 may be used in a first surgical procedure. Illustratively, handle 1300 may be sterilized in a medical autoclave after use in the first surgical procedure and then handle 1300 may be used in a second surgical procedure. In one or more embodiments, handle 1300 may be sterilized in a medical autoclave after use in the second surgical procedure and then handle 1300 may be used in a third surgical procedure.

Figure 14:
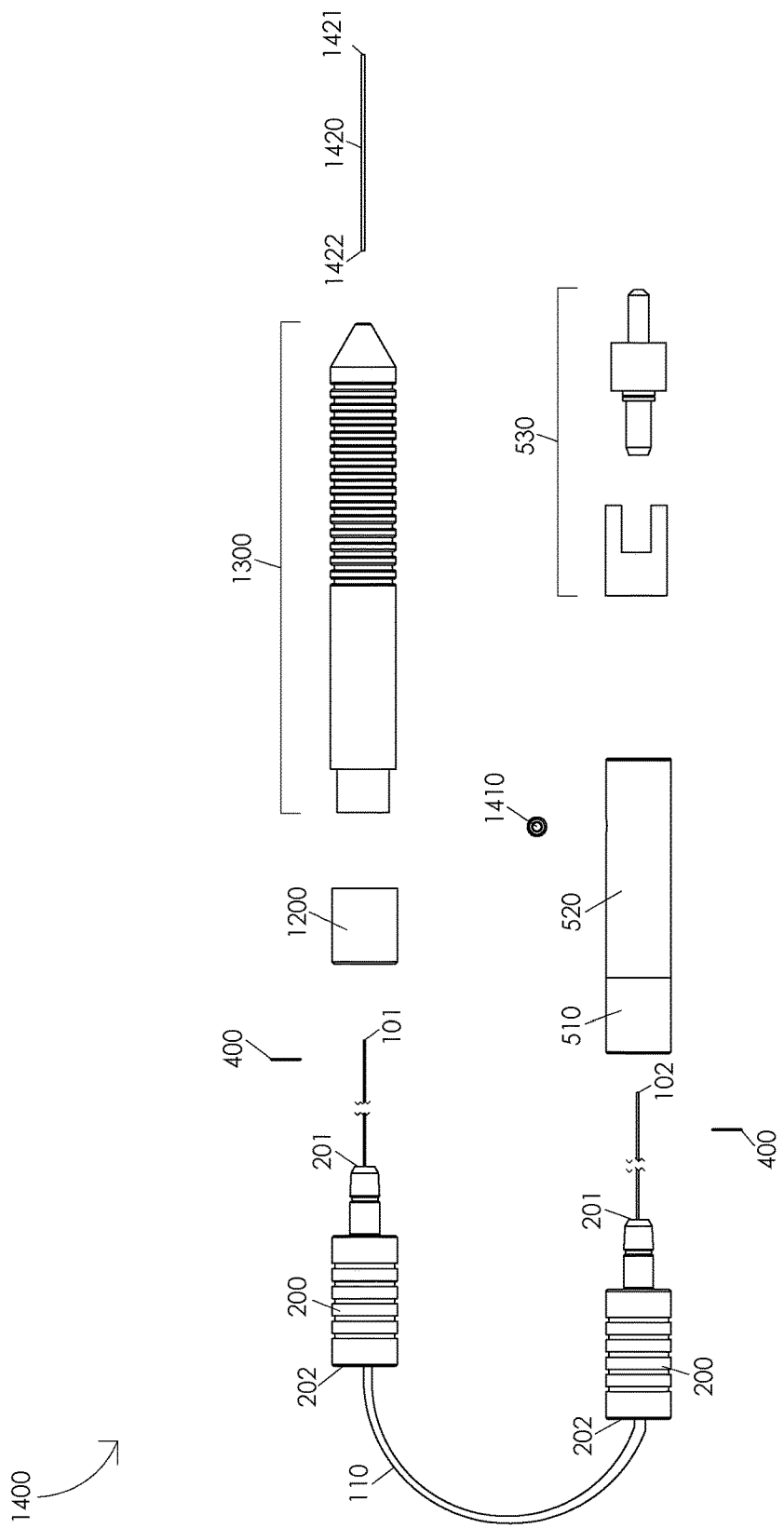
FIG. 14 is a schematic diagram illustrating an exploded view of a straight laser probe with a replaceable optic fiber assembly.

FIG. 14 is a schematic diagram illustrating an exploded view of a straight laser probe with a replaceable optic fiber assembly 1400. In one or more embodiments, a straight laser probe with a replaceable optic fiber assembly 1400 may comprise a machine adapter 500, a replaceable optic fiber 300, a handle adapter 1200, a handle 1300, a straight housing tube 1420 having a straight housing tube distal end 1421 and a straight housing tube proximal end 1422, and a third fixation mechanism 1410. Illustratively, third fixation mechanism 1410 may be configured to fix a portion of machine interface 530 within machine interface housing 526, e.g., third fixation mechanism 1410 may comprise a setscrew configured to fix a portion of machine interface 530 within machine interface housing 526. Straight housing tube 1420 may be manufactured from any suitable material, e.g., polymers, metals, metal alloys, etc., or from any combination of suitable materials. In one or more embodiments, straight housing tube 1420 may be manufactured from a material suitable for sterilization by a medical autoclave. Illustratively, straight housing tube 1420 may be manufactured from a material, e.g., aluminum, titanium, stainless steel, etc., configured to withstand exposure to temperatures, pressures, and ambient conditions present in a medical autoclave without degradation. For example, straight housing tube 1420 may be configured to function normally after exposure in a temperature 250° F. for 15 minutes at an atmospheric pressure of 15 psi. In one or more embodiments, straight housing tube 1420 may be configured to be used in a surgical procedure and then sterilized by a medical autoclave at least three times. Illustratively, straight housing tube 1420 may be configured to be used in a surgical procedure and then sterilized by a medical autoclave more than three times. In one or more embodiments, straight housing tube 1420 may be sterilized in a medical autoclave and then straight housing tube 1420 may be used in a first surgical procedure. Illustratively, straight housing tube 1420 may be sterilized in a medical autoclave after use in the first surgical procedure and then straight housing tube 1420 may be used in a second surgical procedure. In one or more embodiments, straight housing tube 1420 may be sterilized in a medical autoclave after use in the second surgical procedure and then straight housing tube 1420 may be used in a third surgical procedure.

Figure 15:
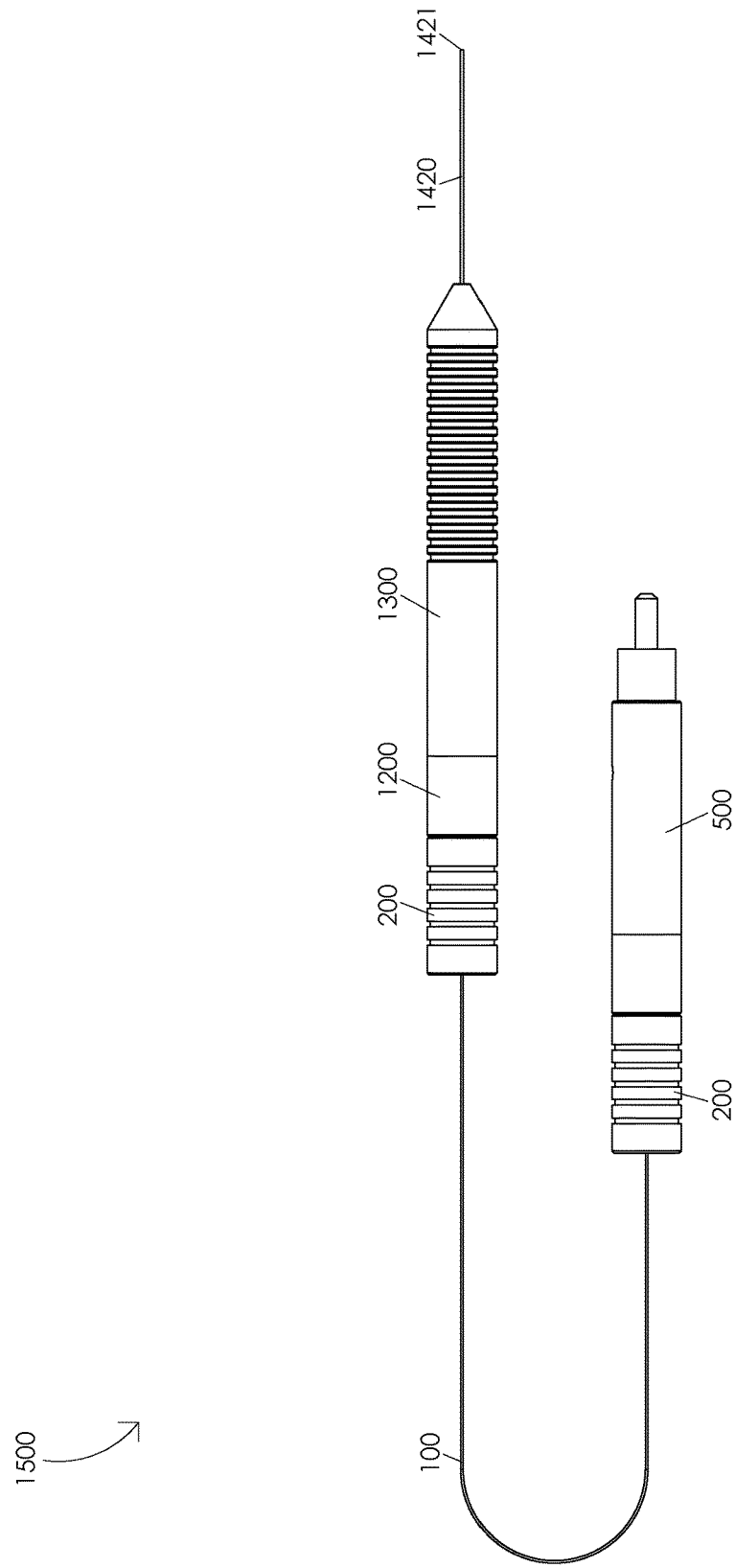
FIG. 15 is a schematic diagram illustrating an assembled straight laser probe with a replaceable optic fiber.

FIG. 15 is a schematic diagram illustrating an assembled straight laser probe with a replaceable optic fiber 1500. Illustratively, a portion of replaceable optic fiber 300 may be disposed within machine adapter 500. In one or more embodiments, optic fiber proximal end 102 may be threaded through machine adapter 500. Illustratively, a portion of replaceable optic fiber 300 may be disposed within machine adapter 500, e.g., optic fiber proximal end 102 may be actuated into end cap proximal taper 514. In one or more embodiments, optic fiber proximal end 102 may be actuated out from end cap proximal taper 514, e.g., optic fiber proximal end 102 may be actuated into end cap inner bore 513. Illustratively, optic fiber proximal end 102 may be actuated out from end cap inner bore 513, e.g., optic fiber proximal end 102 may be actuated into canted coil spring housing 550. In one or more embodiments, optic fiber proximal end 102 may be actuated out from canted coil spring housing 550, e.g., optic fiber proximal end 102 may be actuated into machine adapter base proximal chamber 523. Illustratively, optic fiber proximal end 102 may be actuated out from machine adapter base proximal chamber 523, e.g., optic fiber proximal end 102 may be actuated into machine adapter base guide cone 524. In one or more embodiments, machine adapter base guide cone 524 may be configured to guide a portion of replaceable optic fiber 300 into machine adapter base inner bore 525. Illustratively, optic fiber proximal end 102 may be actuated out from machine adapter base guide cone 524, e.g., optic fiber proximal end 102 may be actuated into machine adapter base inner bore 525. In one or more embodiments, optic fiber proximal end 102 may be actuated out from machine adapter base inner bore 525, e.g., optic fiber proximal end 102 may be actuated into machine interface proximal taper 533. Illustratively, optic fiber proximal end 102 may be actuated out from machine interface proximal taper 533, e.g., optic fiber proximal end 102 may be actuated into machine interface inner bore 534. In one or more embodiments, optic fiber proximal end 102 may be actuated out from machine interface inner bore 534, e.g., optic fiber proximal end 102 may be actuated into machine interface guide cone 535. Illustratively, machine interface guide cone 535 may be configured to guide a portion of replaceable optic fiber 300 into optic fiber proximal end guide 536. In one or more embodiments, optic fiber proximal end 102 may be actuated out from machine interface guide cone 535, e.g., optic fiber proximal end 102 may be actuated into optic fiber proximal end guide 536. For example, a portion of replaceable optic fiber 300 may be disposed within machine adapter 500 wherein optic fiber proximal end 102 may be adjacent to machine adapter distal end 501.

In one or more embodiments, a portion of second connector 200 may be disposed within machine adapter 500. Illustratively, second connector distal end 201 may be actuated into machine adapter 500. In one or more embodiments, second connector distal end 201 may be actuated into end cap proximal taper 514. Illustratively, second connector distal end 201 may be actuated out from end cap proximal taper 514, e.g., second connector distal end 201 may be actuated into end cap inner bore 513. In one or more embodiments, second connector distal end 201 may be actuated out from end cap inner bore 513, e.g., second connector distal end 201 may be actuated into machine adapter base proximal chamber 523. Illustratively, a portion of second connector 200 may be temporarily fixed within machine adapter 500. In one or more embodiments, canted coil spring 400 may be configured to temporarily fix a portion of second connector 200 within machine adapter 500. Illustratively, as second connector distal end 201 is actuated into machine adapter base proximal chamber 523, canted coil spring 400 may interface with a portion of second connector 200, e.g., canted coil spring 400 may interface with temporary fixation channel 205. In one or more embodiments, an interface between canted coil spring 400 and temporary fixation channel 205 may be configured to temporarily fix a portion of second connector 200 within machine adapter 500. Illustratively, a portion of second connector 200 may be temporarily fixed within machine adapter 500, e.g., by a spring force or any suitable temporary fixation means.

In one or more embodiments, a portion of handle 1300 may be disposed within handle adapter 1200, e.g., handle proximal end 1302 may be disposed within handle adapter 1200. Illustratively, a portion of handle 1300 may be disposed within handle proximal end housing 1220, e.g., handle proximal end 1302 may be disposed within handle proximal end housing 1220. In one or more embodiments, handle interface 1225 may be configured to interface with handle adapter interface 1325, e.g., when a portion of handle 1300 is disposed within handle adapter 1200. Illustratively, a portion of handle 1300 may be fixed within handle adapter 1200, e.g., by an adhesive or any suitable fixation means. In one or more embodiments, handle proximal end 1302 may be fixed within handle proximal end chamber 1220, e.g., by a press fit, a setscrew, etc. Illustratively, canted coil spring 400 may be disposed within handle 1300. In one or more embodiments, canted coil spring 400 may be disposed within canted coil spring housing 1350. Illustratively, canted coil spring 400 may be fixed within canted coil spring housing 1350. In one or more embodiments, canted coil spring 400 may be fixed within canted coil spring housing 1350, e.g., by an adhesive or any suitable fixation means. Illustratively, canted coil spring 400 may be fixed within canted coil spring housing 1350, e.g., by a spring force. For example, canted coil spring 400 may be configured to apply a spring force to an outer perimeter of canted coil spring housing 1350. In one or more embodiments, a portion of straight housing tube 1420 may be disposed within handle 1300, e.g., straight housing tube proximal end 1422 may be disposed within handle 1300. Illustratively, a portion of straight housing tube 1420 may be disposed within optic fiber distal end guide 1360, e.g., straight housing tube proximal end 1422 may be disposed within optic fiber distal end guide 1360. In one or more embodiments, a portion of straight housing tube 1420 may be fixed within handle 1300, e.g., straight housing tube proximal end 1422 may be fixed within optic fiber distal end guide 1360. Illustratively, a portion of straight housing tube 1420 may be fixed within optic fiber distal end guide 1360, e.g., by an adhesive or any suitable fixation means. In one or more embodiments, a portion of straight housing tube 1420 may be fixed within optic fiber distal end guide 1360, e.g., by a press fit, a setscrew, etc.

Illustratively, a portion of replaceable optic fiber 300 may be disposed within handle adapter 1200, e.g., a portion of replaceable fiber 300 may be disposed within handle 1300. In one or more embodiments, optic fiber distal end 101 may be threaded through handle adapter 1200, e.g., optic fiber distal end 101 may be threaded into handle adapter proximal end 1202. Illustratively, a portion of replaceable optic fiber 300 may be disposed within handle adapter 1200, e.g., optic fiber distal end 101 may be actuated into handle adapter taper 1214. In one or more embodiments, optic fiber distal end 101 may be actuated out from handle adapter taper 1214, e.g., optic fiber distal end 101 may be actuated into handle adapter chamber 1213. Illustratively, optic fiber distal end 101 may be actuated out from handle adapter chamber 1213, e.g., optic fiber distal end 101 may be actuated into handle proximal chamber 1330. In one or more embodiments, optic fiber distal end 101 may be actuated out from handle proximal chamber 1330, e.g., optic fiber distal end 101 may be actuated into canted coil spring housing 1350. In one or more embodiments, optic fiber distal end 101 may be actuated out from canted coil spring housing 1350, e.g., optic fiber distal end 101 may be actuated into handle taper 1335. Illustratively, optic fiber distal end 101 may be actuated out from handle taper 1335, e.g., optic fiber distal end 101 may be actuated into handle inner bore 1340. In one or more embodiments, optic fiber distal end 101 may be actuated out from handle inner bore 1340, e.g., optic fiber distal end 101 may be actuated into handle guide cone 1345. Illustratively, handle guide cone 1345 may be configured to guide a portion of replaceable optic fiber 300 into optic fiber distal end guide 1360, e.g., handle guide cone 1345 may be configured to guide optic fiber distal end 101 into optic fiber distal end guide 1360. In one or more embodiments, optic fiber distal end 101 may be actuated out from handle guide cone 1345, e.g., optic fiber distal end 101 may be actuated into optic fiber distal end guide 1360. Illustratively, optic fiber distal end 101 may be actuated out from optic fiber distal end guide 1360, e.g., optic fiber distal end 101 may be actuated into straight housing tube 1420. In one or more embodiments, a portion of replaceable optic fiber 300 may be actuated into handle 1300 wherein optic fiber distal end 101 may be adjacent to straight housing tube distal end

1421. Illustratively, a portion of replaceable optic fiber 300 may be disposed within straight housing tube 1420 wherein optic fiber distal end 101 may be adjacent to straight housing tube distal end 1421.

In one or more embodiments, a portion of first connector 200 may be disposed within handle adapter 1200, e.g., a portion of first connector 200 may be disposed within handle 1300. Illustratively, first connector distal end 201 may be actuated into handle adapter 1200. In one or more embodiments, first connector distal end 201 may be actuated into handle adapter taper 1214. Illustratively, first connector distal end 201 may be actuated out from handle proximal taper 1214, e.g., first connector distal end 201 may be actuated into handle adapter chamber 1213. In one or more embodiments, first connector distal end 201 may be actuated out from handle adapter chamber 1213, e.g., first connector distal end 201 may be actuated into handle proximal chamber 1330. Illustratively, a portion of first connector 200 may be temporarily fixed within handle adapter 1200, e.g., a portion of first connector 200 may be temporarily fixed within handle 1300. In one or more embodiments, canted coil spring 400 may be configured to temporarily fix a portion of first connector 200 within handle adapter 1200, e.g., canted coil spring 400 may be configured to temporarily fix a portion of first connector 200 within handle 1300. Illustratively, as first connector distal end 201 is actuated into handle proximal chamber 1330, canted coil spring 400 may interface with a portion of first connector 200, e.g., canted coil spring 400 may interface with temporary fixation channel 205. In one or more embodiments, an interface between canted coil spring 400 and temporary fixation channel 205 may be configured to temporarily fix a portion of first connector 200 within handle adapter 1200, e.g., an interface between canted coil spring 400 and temporary fixation channel 205 may be configured to temporarily fix a portion of first connector within handle 1300. Illustratively, a portion of first connector 200 may be temporarily fixed within handle adapter 1200, e.g., by a spring force or any suitable temporary fixation means. In one or more embodiments, a portion of first connector 200 may be temporarily fixed within handle 1300, e.g., by a spring force or any suitable temporary fixation means.

In one or more embodiments, replaceable optic fiber 300 may comprise a single use, disposable medical device, e.g., replaceable optic fiber 300 may be sold as a sterile product. Illustratively, replaceable optic fiber 300 may be sold as a sterile product in a hermetically sealed package, e.g., sterilized by ethylene oxide sterilization. In one or more embodiments, replaceable optic fiber 300 may be configured for use in a single surgical procedure, e.g., a new replaceable optic fiber 300 may be required for each surgical procedure. Illustratively, machine adapter 500 may comprise a reusable medical device, e.g., machine adapter 500 may be sold as a non-sterile product. In one or more embodiments, handle adapter 1200 may comprise a reusable medical device, e.g., handle adapter 1200 may be sold as a non-sterile product. Illustratively, handle 1300 and straight housing tube 1420 may comprise a single reusable medical device, e.g., handle 1300 and straight housing tube 1420 may be sold as a non-sterile product.

In one or more embodiments, machine adapter 500, handle adapter 1200, handle 1300, and straight housing tube 1420 may be sterilized a first time, e.g., by a medical autoclave. Illustratively, a first replaceable fiber 300 hermetically sealed package may be opened to prepare for a first surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into handle adapter 1200, e.g., first connector 200 may be temporarily fixed within handle adapter 1200. Illustratively, a surgeon may then perform a first surgical procedure, e.g. a surgeon may perform a photocoagulation surgical procedure. After performing the first surgical procedure, the first replaceable optic fiber 300 may be discarded, e.g., second connector 200 may be removed from machine adapter 500, first connector 200 may be removed from handle adapter 1200, and the first replaceable optic fiber 300 may be placed in a medical waste disposal bin. In one or more embodiments, machine adapter 500, handle adapter 1200, handle 1300, and straight housing tube 1420 may be sterilized a second time, e.g., by a medical autoclave. Illustratively, a second replaceable fiber 300 hermetically sealed package may be opened to prepare for a second surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into handle adapter 1200, e.g., first connector 200 may be temporarily fixed within handle adapter 1200. Illustratively, a surgeon may then perform a second surgical procedure, e.g. a surgeon may perform a photocoagulation surgical procedure. After performing the second surgical procedure, the second replaceable optic fiber 300 may be discarded, e.g., second connector 200 may be removed from machine adapter 500, first connector 200 may be removed from handle adapter 1200, and the second replaceable optic fiber 300 may be placed in a medical waste disposal bin. In one or more embodiments, machine adapter 500, handle adapter 1200, handle 1300, and straight housing tube 1420 may be sterilized a third time, e.g., by a medical autoclave. Illustratively, a third replaceable fiber 300 hermetically sealed package may be opened to prepare for a third surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into handle adapter 1200, e.g., first connector 200 may be temporarily fixed within handle adapter 1200. Illustratively, a surgeon may then perform a third surgical procedure, e.g. a surgeon may perform a photocoagulation surgical procedure. After performing the third surgical procedure, the third replaceable optic fiber 300 may be discarded, e.g., second connector 200 may be removed from machine adapter 500, first connector 200 may be removed from handle adapter 1200, and the third replaceable optic fiber 300 may be placed in a medical waste disposal bin.

Figure 16:
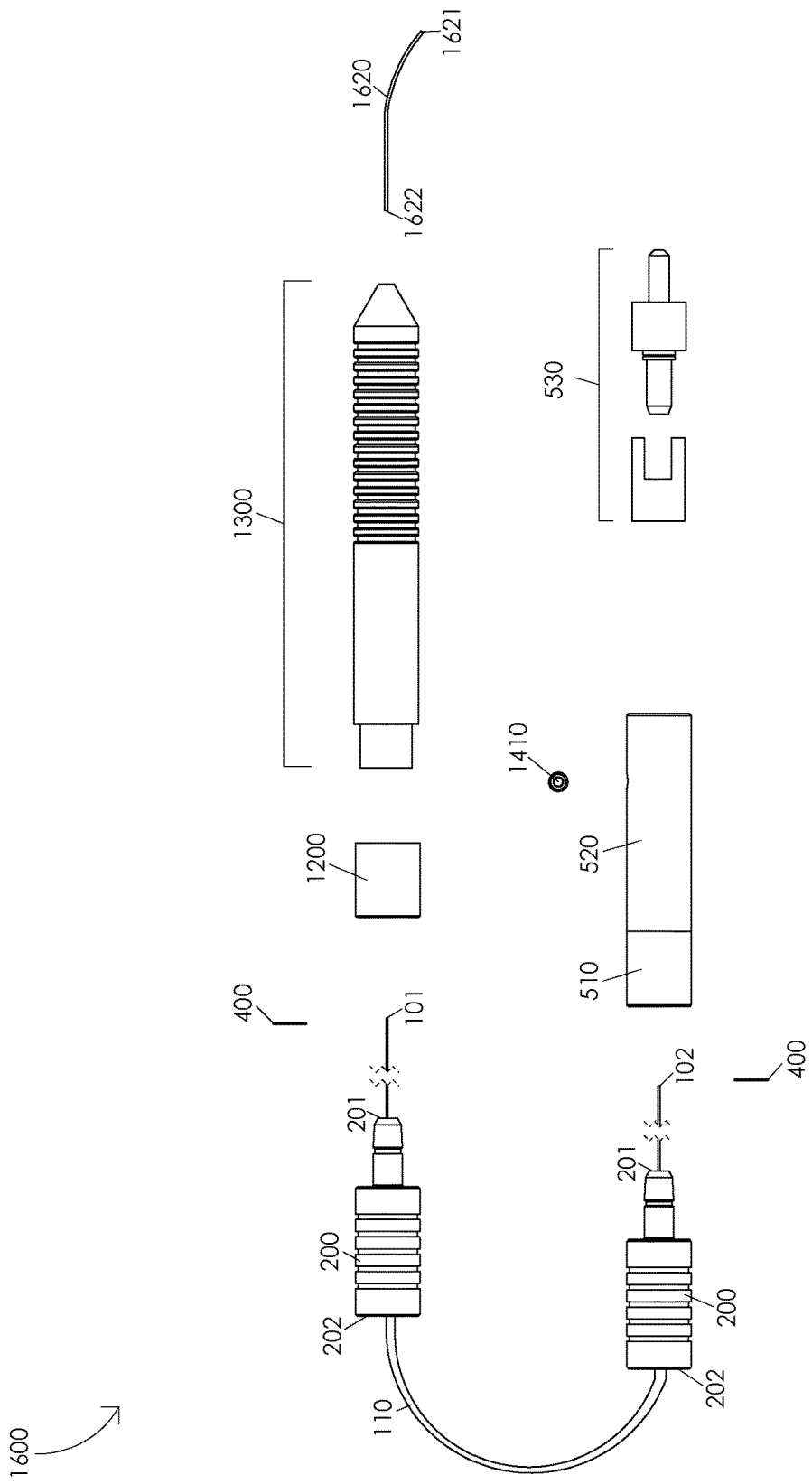
FIG. 16 is a schematic diagram illustrating an exploded view of a curved laser probe with a replaceable optic fiber assembly.

FIG. 16 is a schematic diagram illustrating an exploded view of a curved laser probe with a replaceable optic fiber assembly 1600. In one or more embodiments, a curved laser probe with a replaceable optic fiber assembly 1600 may comprise a machine adapter 500, a replaceable optic fiber 300, a handle adapter 1200, a handle 1300, a curved housing tube 1620 having a curved housing tube distal end 1621 and a curved housing tube proximal end 1622, and a third fixation mechanism 1410. Illustratively, third fixation mechanism 1410 may be configured to fix a portion of machine interface 530 within machine interface housing 526, e.g., third fixation mechanism 1410 may comprise a setscrew configured to fix a portion of machine interface 530 within machine interface housing 526. Curved housing tube 1620 may be manufactured from any suitable material, e.g., polymers, metals, metal alloys, etc., or from any combination of suitable materials. In one or more embodiments, curved housing tube 1620 may be manufactured from a material suitable for sterilization by a medical autoclave. Illustratively, curved housing tube 1620 may be manufactured from a material, e.g., aluminum, titanium, stainless steel, etc., configured to withstand exposure to temperatures, pressures, and ambient conditions present in a medical autoclave without degradation. For example, curved housing tube 1620 may be configured to function normally after exposure in a temperature 250° F. for 15 minutes at an atmospheric pressure of 15 psi. In one or more embodiments, curved housing tube 1620 may be configured to be used in a surgical procedure and then sterilized by a medical autoclave at least three times. Illustratively, curved housing tube 1620 may be configured to be used in a surgical procedure and then sterilized by a medical autoclave more than three times. In one or more embodiments, curved housing tube 1620 may be sterilized in a medical autoclave and then curved housing tube 1620 may be used in a first surgical procedure. Illustratively, curved housing tube 1620 may be sterilized in a medical autoclave after use in the first surgical procedure and then curved housing tube 1620 may be used in a second surgical procedure. In one or more embodiments, curved housing tube 1620 may be sterilized in a medical autoclave after use in the second surgical procedure and then curved housing tube 1620 may be used in a third surgical procedure.

Figure 17:
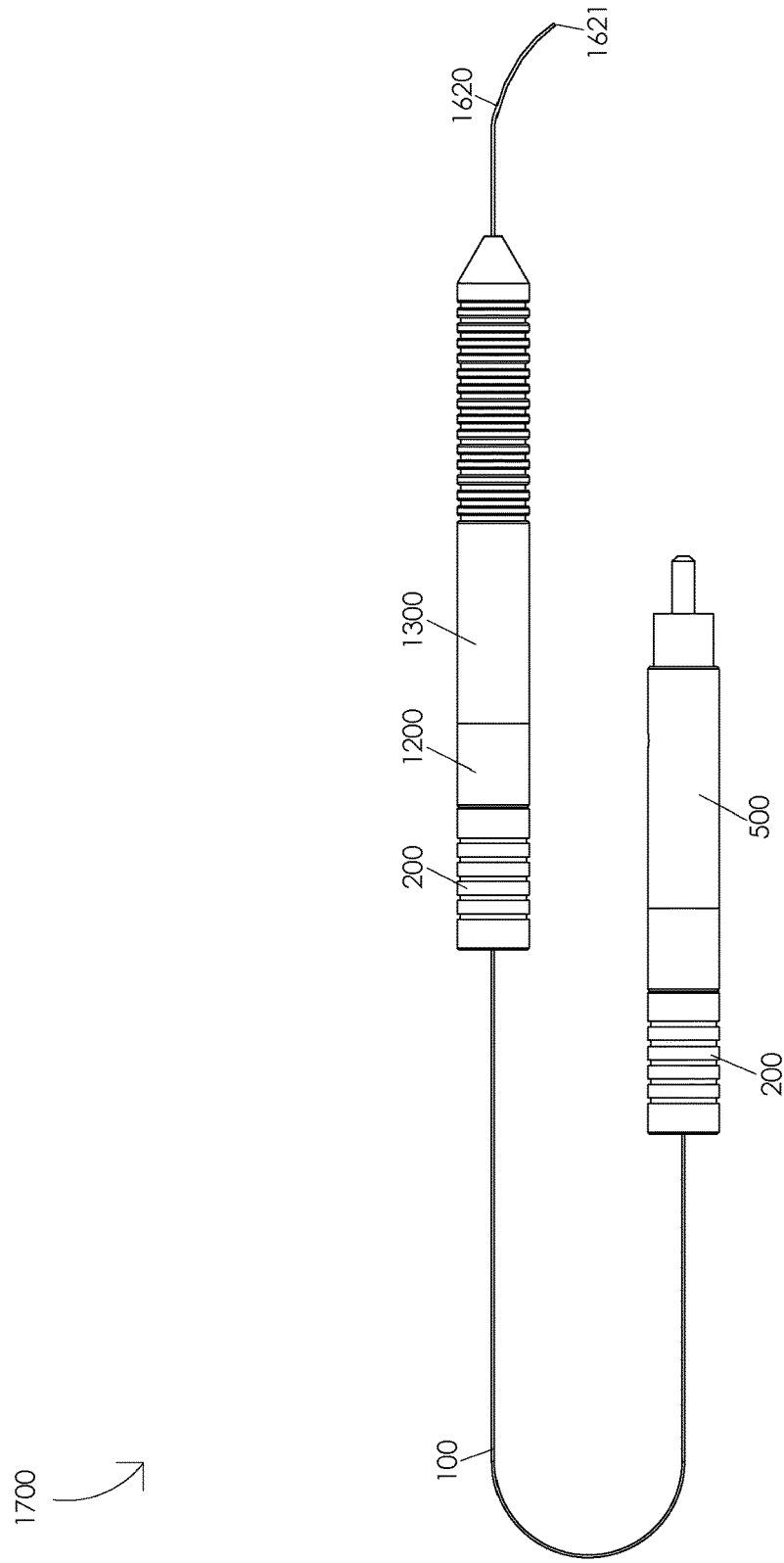
FIG. 17 is a schematic diagram illustrating an assembled curved laser probe with a replaceable optic fiber.

FIG. 17 is a schematic diagram illustrating an assembled curved laser probe with a replaceable optic fiber 1700. Illustratively, a portion of curved housing tube 1620 may be disposed within optic fiber distal end guide 1360, e.g., curved housing tube proximal end 1622 may be disposed within optic fiber distal end guide 1360. In one or more embodiments, a portion of curved housing tube 1620 may be fixed within optic fiber distal end guide 1360, e.g., by an adhesive or any suitable fixation means. Illustratively, second connector 200 may be temporarily fixed within machine adapter 500. In one or more embodiments first connector 200 may be temporarily fixed within handle adapter 1200 and handle 1300. Illustratively, a portion of replaceable optic fiber 300 may be disposed within curved housing tube 1620 wherein optic fiber distal end 101 may be adjacent to curved housing tube distal end 1621.

In one or more embodiments, replaceable optic fiber 300 may comprise a single use, disposable medical device, e.g., replaceable optic fiber 300 may be sold as a sterile product. Illustratively, replaceable optic fiber 300 may be sold as a sterile product in a hermetically sealed package, e.g., sterilized by ethylene oxide sterilization. In one or more embodiments, replaceable optic fiber 300 may be configured for use in a single surgical procedure, e.g., a new replaceable optic fiber 300 may be required for each surgical procedure. Illustratively, machine adapter 500 may comprise a reusable medical device, e.g., machine adapter 500 may be sold as a non-sterile product. In one or more embodiments, handle adapter 1200 may comprise a reusable medical device, e.g., handle adapter 1200 may be sold as a non-sterile product. Illustratively, handle 1300 and straight housing tube 1420 may comprise a single reusable medical device, e.g., handle 1300 and curved housing tube 1620 may be sold as a non-sterile product.

In one or more embodiments, machine adapter 500, handle adapter 1200, handle 1300, and curved housing tube 1620 may be sterilized a first time, e.g., by a medical autoclave. Illustratively, a first replaceable fiber 300 hermetically sealed package may be opened to prepare for a first surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into handle adapter 1200, e.g., first connector 200 may be temporarily fixed within handle adapter 1200. Illustratively, a surgeon may then perform a first surgical procedure, e.g. a surgeon may perform a photocoagulation surgical procedure. After performing the first surgical procedure, the first replaceable optic fiber 300 may be discarded, e.g., second connector 200 may be removed from machine adapter 500, first connector 200 may be removed from handle adapter 1200, and the first replaceable optic fiber 300 may be placed in a medical waste disposal bin. In one or more embodiments, machine adapter 500, handle adapter 1200, handle 1300, and curved housing tube 1620 may be sterilized a second time, e.g., by a medical autoclave. Illustratively, a second replaceable fiber 300 hermetically sealed package may be opened to prepare for a second surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into handle adapter 1200, e.g., first connector 200 may be temporarily fixed within handle adapter 1200. Illustratively, a surgeon may then perform a second surgical procedure, e.g. a surgeon may perform a photocoagulation surgical procedure. After performing the second surgical procedure, the second replaceable optic fiber 300 may be discarded, e.g., second connector 200 may be removed from machine adapter 500, first connector 200 may be removed from handle adapter 1200, and the second replaceable optic fiber 300 may be placed in a medical waste disposal bin. In one or more embodiments, machine adapter 500, handle adapter 1200, handle 1300, and curved housing tube 1620 may be sterilized a third time, e.g., by a medical autoclave. Illustratively, a third replaceable fiber 300 hermetically sealed package may be opened to prepare for a third surgical procedure. In one or more embodiments, second connector 200 may be inserted into machine adapter 500, e.g., second connector 200 may be temporarily fixed within machine adapter 500. Illustratively, machine adapter 500 may be configured to align optic fiber proximal end 102 with a surgical machine light output. In one or more embodiments, first connector 200 may be inserted into handle adapter 1200, e.g., first connector 200 may be temporarily fixed within handle adapter 1200. Illustratively, a surgeon may then perform a third surgical procedure, e.g. a surgeon may perform a photocoagulation surgical procedure. After performing the third surgical procedure, the third replaceable optic fiber 300 may be discarded, e.g., second connector 200 may be removed from machine adapter 500, first connector 200 may be removed from handle adapter 1200, and the third replaceable optic fiber 300 may be placed in a medical waste disposal bin.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. A device comprising:
a machine adapter having a machine adapter distal end and a machine adapter proximal end, the machine adapter configured to interface with an ophthalmic laser to perform a laser photocoagulation procedure;
a machine adapter inner bore of the machine adapter;
a machine interface of the machine adapter, the machine interface disposed between the
machine adapter distal end and the machine adapter inner bore;
a handle adapter having a handle adapter distal end and a handle adapter proximal end;
an actuation handle having a plurality of actuation arms and a plurality of extension mechanisms;
a replaceable optic fiber;
a pair of connectors of the replaceable optic fiber;
a housing tube having a housing tube distal end and a housing tube proximal end wherein the optic fiber distal end is adjacent to the housing tube distal end;
a first connector of the pair of connectors having a first connector distal end, a first connector proximal end, a first temporary fixation channel, a first interface, a first connector inner bore, a first connector guide cone, and a first optic fiber housing wherein a portion of the first connector is disposed within the handle adapter;
a second connector of the pair of connectors having a second connector distal end, a second connector proximal end, a second temporary fixation channel, a second interface, a second connector inner bore, a second connector guide cone, and a second optic fiber housing wherein a portion of the second connector is disposed within the machine adapter wherein the second connector is identical to the first connector; and
an optic fiber of the replaceable optic fiber having an optic fiber distal end, an optic fiber proximal end, a core, a cladding, and a polyimide buffer wherein the optic fiber is disposed within the first connector and the second connector wherein the optic fiber distal end extends a distal extension distance from the first connector distal end and the optic fiber proximal end extends a proximal extension distance from the second connector distal end wherein the distal extension distance is equal to the proximal extension distance and wherein the optic fiber is fixed in the first connector and wherein the optic fiber is fixed in the second connector and wherein a portion of the replaceable optic fiber is disposed in the machine adapter wherein the optic fiber proximal end is adjacent to the machine adapter distal end.

2. The device of claim 1 wherein the replaceable fiber is sterilized by ethylene oxide sterilization.

3. The device of claim 2 wherein the machine adapter is sterilized by a medical autoclave.

4. The device of claim 2 wherein the handle adapter is sterilized by a medical autoclave.

5. The device of claim 1 further comprising:
a canted coil spring of the handle adapter, the canted coil spring disposed in a canted coil spring housing of the handle adapter.

6. The device of claim 1 wherein the portion of the first connector disposed within the handle adapter is temporarily fixed within the handle adapter.

7. The device of claim 1 further comprising:
a canted coil spring of the machine adapter, the canted coil spring disposed in a canted coil spring housing of the handle adapter.

8. The device of claim 1 wherein the portion of the first connector disposed within the machine adapter is temporarily fixed within the machine adapter.

9. The device of claim 1 wherein the distal extension distance is in a range of 5.0 to 15.0 centimeters.

10. The device of claim 1 wherein the proximal extension distance is in a range of 3.0 to 10.0 centimeters.

11. The device of claim 1 further comprising:
an end cap of the machine adapter; and
a machine adapter base of the machine adapter.

12. The device of claim 11 further comprising:
an end cap inner bore of the machine adapter;
a canted coil spring housing of the machine adapter; and
a machine adapter base guide cone of the machine adapter.

13. The device of claim 12 further comprising:
a machine interface guide cone of the machine adapter; and
an optic fiber proximal end guide of the machine adapter.

14. The device of claim 1 further comprising:
a handle adapter proximal chamber of the handle adapter;
a canted coil spring housing of the handle adapter; and
a handle adapter guide cone of the handle adapter.

15. The device of claim 1 further comprising:
a handle interface of the handle adapter, the handle interface configured to interface with a proximal end of a handle; and
a handle adapter projection of the handle adapter, the handle adapter projection configured to be disposed within a handle adapter housing of the handle.

16. The device of claim 1 further comprising:
a handle adapter chamber of the handle adapter; and
a handle proximal end housing of the handle adapter, the handle proximal end housing configured to house a proximal end of a handle.

17. The device of claim 1 further comprising:
a jacket of the replaceable optic fiber wherein the jacket is disposed over a portion of the optic fiber.

* * * * *